(12) United States Patent
Pardey et al.

(10) Patent No.: US 10,383,604 B2
(45) Date of Patent: Aug. 20, 2019

(54) DATA ANALYSIS SYSTEM AND METHOD

(71) Applicants: James Pardey, Gallows Hill (GB); Robert Milnes, Gallows Hill (GB)

(72) Inventors: James Pardey, Gallows Hill (GB); Robert Milnes, Gallows Hill (GB)

(73) Assignee: FERTILITY FOCUS LIMITED, Warwick (GB)

( * ) Notice: Subject to any disclaimer, the term of this patent is extended or adjusted under 35 U.S.C. 154(b) by 561 days.

(21) Appl. No.: 14/900,661

(22) PCT Filed: Jun. 27, 2014

(86) PCT No.: PCT/GB2014/051976
§ 371 (c)(1),
(2) Date: Dec. 22, 2015

(87) PCT Pub. No.: WO2014/207484
PCT Pub. Date: Dec. 31, 2014

(65) Prior Publication Data
US 2016/0143630 A1     May 26, 2016

(30) Foreign Application Priority Data

Jun. 27, 2013  (GB) .................................. 1311580.3
Mar. 20, 2014  (GB) .................................. 1405016.5

(51) Int. Cl.
*A61B 5/00*     (2006.01)
*A61B 10/00*    (2006.01)
*A61B 5/01*     (2006.01)

(52) U.S. Cl.
CPC ........ *A61B 10/0012* (2013.01); *A61B 5/0008* (2013.01); *A61B 5/01* (2013.01);
(Continued)

(58) Field of Classification Search
CPC .................. A61B 5/01; A61B 10/0012; A61B 2010/0019; A61B 5/0008; A61B 5/7203; A61B 5/7278; A61B 5/7282
See application file for complete search history.

(56) References Cited

U.S. PATENT DOCUMENTS 5,050,612 A     9/1991  Matsumura
9,119,602 B2 *  9/2015  Schafer .............. A61B 10/0012
(Continued)

FOREIGN PATENT DOCUMENTS

WO     WO-2008029130 A2    3/2008
WO     WO-2011070577 A2    6/2011

OTHER PUBLICATIONS

Search Report Under Section 17(5) issued by the UK Intellectual Property Office in relation to UK Application No. GB1405016.5 dated Jan. 29, 2015 (5 pages).
(Continued)

*Primary Examiner* — Max F Hindenburg
(74) *Attorney, Agent, or Firm* — Robert P. Michal, Esq.; Carter, DeLuca & Farrell LLP

(57) ABSTRACT

A method and apparatus for determining at least one representative temperature value for a female human user for an extended period includes receiving at least a first, a second and a third plurality of temperature measurements obtained from a female human user during at least first, second and third respective extended periods, wherein each extended period includes at least one hour and wherein the start of each extended period is separated by at least 8 hours. At least one representative temperature value is calculated for the second extended period. The representative temperature value is calculated using at least one first temperature value obtained from a plurality of measurements taken during the first extended period, at least one second temperature value obtained from a plurality of measurements taken during the
(Continued)

second extended period and at least one third temperature value obtained from a plurality of measurements taken during the third extended period.

20 Claims, 9 Drawing Sheets

(52) U.S. Cl.
CPC .......... *A61B 5/7203* (2013.01); *A61B 5/7278* (2013.01); *A61B 5/7282* (2013.01); *A61B 2010/0019* (2013.01)

(56) References Cited

U.S. PATENT DOCUMENTS

| | | | |
|---|---|---|---|
| 9,155,523 B2* | 10/2015 | James | A61B 10/0012 |
| 9,592,033 B2* | 3/2017 | Toriumi | A61B 5/746 |
| 2008/0029130 A1 | 2/2008 | Concar et al. | |
| 2009/0326410 A1 | 12/2009 | James et al. | |

OTHER PUBLICATIONS

Search Report Under Section 17(5) issued by the UK Intellectual Property Office in relation to UK Application No. GB1311580.3 dated Dec. 17, 2013 (5 pages).

International Search Report and Written Opinion of the International Searching Authority issued by the European Patent Office in relation to International Application No. PCT/GB2014/051976 dated Sep. 16, 2014 (5 pages).

\* cited by examiner

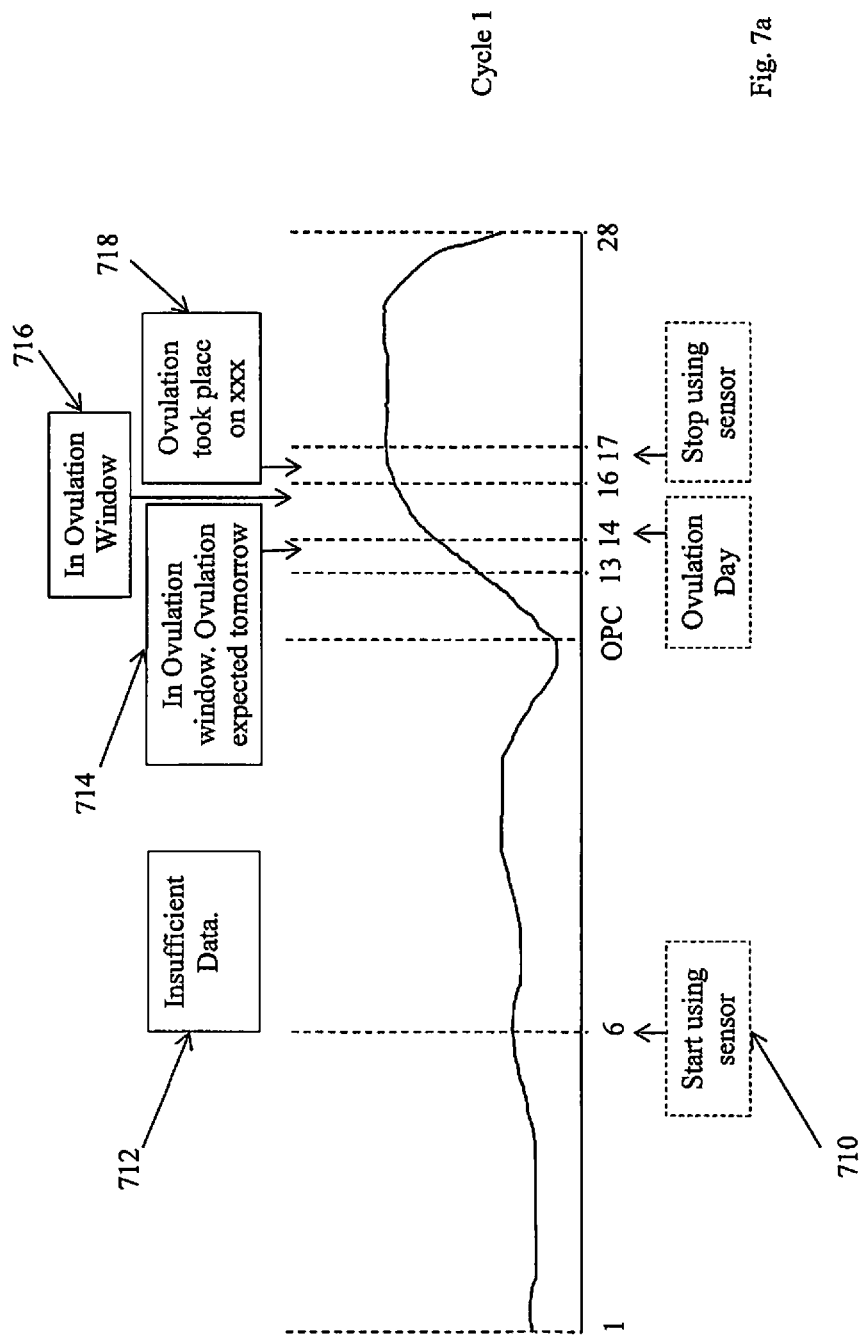

DATA ANALYSIS SYSTEM AND METHOD

CROSS-REFERENCE TO RELATED APPLICATIONS

This application is a National Phase Entry under 35 USC § 371 of PCT Patent Application Serial No. PCT/GB2014/051976 filed Jun. 27, 2014, which claims the benefit under 35 USC § 119(e) to UK Patent Application No. 1311580.3, filed Jun. 27, 2013 and UK Patent Application No. 1405016.5 filed Mar. 20, 2014, the disclosure of each of these applications are expressly incorporated herein by reference in their entireties.

It has long been known that body temperature varies as hormone levels change throughout the menstrual cycle of a female mammal. It has been appreciated that, in theory, this phenomenon can provide a useful indicator of the fertility of the mammal and, in particular, this can be useful in assessing female human fertility. The basal body temperature is the temperature of the body "at rest" and reflects variations in the body temperature due to changing hormone levels and other cyclical factors. The basal body temperature can be most accurately measured while the user is asleep or immediately upon waking, before there is significant movement or activity by the user.

However, except under carefully-controlled conditions, the changes in basal body temperature throughout a cycle can still be quite small relative to the effects of noise in the data.

Development of an intra-vaginal temperature sensor and methods of operation have enabled the frequent collection of more accurate temperature data. The collection and use of such data is discussed in International Patent Publication No. WO-A2-2008/029130, which is incorporated by reference herein in its entirety. However, significant amounts of noise are still seen within the data. Such noise may occur due to factors such as variations in the placement of the thermometer, variations in the health or activity level of the female and external environmental factors.

Noise in the data can make it difficult to see the details of all of the temperature changes that arise during a cycle. It can therefore be difficult to use this data to obtain an accurate picture of the fertility level of the female user.

Once temperature data has been obtained, a common way of determining an ovulation event within the female mammal is the "3 over 6 rule" in which an ovulation event is indicated when three consecutive representative temperature values are registered, all of which are above the average of the representative temperature values of the last six preceding days. WO-A2-2008/029130 describes a "3 over 3 rule" which can enable ovulation to be detected even if data is not available for all 6 preceding days. However, using such methods, it is clear that an ovulation event cannot be indicated until at least 3-4 days after a temperature rise has started. While these methods can provide a useful and accurate indication of when an ovulation event may occur during the next cycle, the indication is usually too late for fertilisation of an egg to occur within the present menstrual cycle.

According to one aspect, there is provided a method of determining at least one representative temperature value for a female human user for an extended period, the method comprising: receiving at least a first, a second and a third plurality of temperature measurements obtained from a female human user during at least first, second and third respective extended periods, wherein each extended period comprises at least one hour and wherein the start of each extended period is separated by at least 8 hours;

calculating at least one representative temperature value for the second extended period, wherein the representative temperature value is calculated using:

at least one first temperature value obtained from a plurality of measurements taken during the first extended period;

at least one second temperature value obtained from a plurality of measurements taken during the second extended period; and at least one third temperature value obtained from a plurality of measurements taken during the third extended period.

The use of data from preceding and following extended periods to determine a representative temperature value for a particular extended period can increase the accuracy of the representative temperature value. It may be counter-intuitive to use data from outside the extended period if the aim is to obtain a representative temperature value for the user within a particular extended period. However, it has been found that data obtained across several days can be particularly useful to stabilise temperature readings across extended periods.

Optionally, each extended period comprises at least two time windows and a representative temperature value is calculated for each time window.

In some embodiments, the representative temperature value for the second extended period is based on at least two temperature values obtained from temperature measurements taken during the first extended period and at least one temperature value obtained from temperature measurements taken during the third extended period.

Optionally, a second representative temperature value for the second extended period is based on at least one temperature value obtained from temperature measurements taken during the first extended period and on at least two temperature values obtained from temperature measurements taken during the third extended period.

In one embodiment, the representative temperature value for the second extended period comprises an average of the at least one first, at least one second and at least one third temperature values. The average may be weighted based on the number of measurements taken during the respective first, second and third extended periods, or during time windows specified within those extended periods.

In one embodiment, the at least one first, second and third values comprise average temperature values for the first, second and third extended periods respectively.

Optionally, each extended period is divided into a plurality of time windows and wherein a representative temperature value is obtained for each time window of each extended period.

Optionally, each extended period is divided into a plurality of time windows and wherein the at least one first temperature value, at least one second temperature value and at least one third temperature value comprise readings obtained in corresponding time windows in the respective first, second and third extended periods.

The method may further comprise weighting the calculation of the representative temperature value based on the number of readings in the first, second and third time windows of the respective extended periods.

The method may further include calculating the at least one representative temperature value for the second extended period using a temperature value obtained for at least one extended period prior to the first extended period.

Optionally, the method further includes calculating the at least one representative temperature value for the second extended period using a temperature value obtained for at least one extended period subsequent to the third extended period.

The method may also include filtering the temperature data to disregard faulty or irrelevant data and/or correcting at least one non-disregarded temperature reading for diurnal temperature variation.

Optionally, the method may further include filtering the temperature measurements prior to calculating the representative temperature values, wherein filtering comprises removing faulty or irrelevant measurements, preferably wherein filtering further comprises removing the maximum and minimum temperature measurements from the measurements obtained during the extended period.

Optionally, the method further includes calculating at least one representative temperature value for each at least three, preferably at least five, extended periods, optionally, analysing the representative temperature values to identify an indication of a temperature change event for the female human user and further optionally, providing to the user an indication of timing of an ovulation event based on the identification of the indication of a temperature change event.

According to a further aspect, there is provided a method of identifying a temperature change event for a female human user, the method comprising:
receiving temperature data for the female human user for a plurality of extended periods, each extended period comprising at least 6 hours, the beginning of one extended period being separated from the beginning of a subsequent and a preceding extended period by at least 18 hours;
determining at least one representative temperature value for each extended period based on at least the received temperature data for that extended period;
assessing a plurality of consecutive representative temperature values using a first method to determine whether a temperature change event occurred 4 or more days prior to the extended period;
assessing a plurality of consecutive representative temperature values using a second method, different from the first method, to determine whether a temperature change event occurred fewer than 4 days prior to the extended period.

It has been appreciated that data can be assessed by applying different algorithms or techniques to determine whether a temperature change event occurred at different times preceding the current extended period. That is, a first technique or method may more accurately determine whether a temperature change event occurred within the preceding 4 days, whereas a second technique or method may be more useful in determining whether a temperature change event occurred more than 4 days ago. By applying both techniques to the same data, the method can detect whether the data indicates a temperature change event fewer than or more than 4 days ago.

The first method can be used to give a more precise retrospective indication of whether a temperature change event occurred in the data more than 4 days ago. This can be helpful since the second method, which aims to give an earlier, but probably less certain, indication of a temperature change event may miss the temperature change event in the data. Providing a first, more accurate method can indicate to the user the existence of a temperature change event, and so an ovulation event. Even if this indication comes too late in the present cycle to predict ovulation in that cycle, an indication of an ovulation event having taken place can enable the user to desist from taking any further temperature readings in the current cycle, until after they have next menstruated. A retrospective determination of a temperature change event, and so ovulation event, can also be useful information for a user or their medical care worker, for example in confirming that the user is ovulating, in charting the ovulation dates of the user, and to some extent, in providing an indication of when a user might next ovulate. Such information may also be fed back into the assessment method to determine the next ovulation date of the user.

Examples of first and second methods that can be used for assessing the representative temperature values are set out in more detail herein, in particular in the following aspects. Steps and features of those aspects may be implemented in conjunction with the present aspect in order to identify a temperature change event.

Optionally, the first method comprises determining whether the change in representative temperature value from at least one reference value, preferably a plurality of reference values is greater than a predetermined threshold.

The reference value may be derived from at least one representative temperature value obtained for the user four or more extended periods previously.

Optionally, the first method includes determining whether consecutive representative temperature values differ by greater than a predetermined threshold value for a plurality of consecutive representative temperature values.

The second method may also include assessing the change in the representative temperature values over time against a plurality of criteria.

Optionally, assessing comprises allocating a score to each criterion that is met.

The method optionally further includes determining a cumulative score and making an assessment of whether a temperature change event occurred fewer than 4 days prior to the extended period based on whether the total score is greater than a predetermined value.

Optionally, the method also includes determining whether a temperature change event occurred further comprises providing information to the user derived from the determination of the temperature change event. Preferably, the information provided to the user comprises an indication that the user has ovulated or is about to ovulate, preferably further comprising an indication of the date of ovulation of the user.

The method may further include providing an indication to the user that they should desist from obtaining further temperature data within the current menstrual cycle.

According to a further aspect, there is provided a method of identifying a temperature change event for a female human user, the method comprising:
receiving temperature data for the female human user for a plurality of extended periods, each extended period comprising at least 6 hours, the beginning of one extended period being separated from the beginning of a subsequent and a preceding extended period by at least 18 hours;
dividing the temperature data received for each extended period into at least two time windows;
determining a representative temperature value for each time window based on at least the received temperature data for that time window;
assessing a change in the representative temperature value associated with the first time window;
determining whether a temperature change event occurred in any of at least two preceding extended periods based on the change in the representative temperature value;
assessing a change in the representative temperature value associated with the second time window;

determining whether a temperature change event occurred in any of at least two preceding extended periods based on the change in the representative temperature value.

Hence the data is assessed each time a new representative temperature value is determined for a new time window of an extended period. This can enable a temperature change event to be detected as soon as sufficient data is available, even if this is within a single night's data. Further, the temperature change event may be detected at any time during the cycle and not just at times when it might be expected, for example as determined by charting or by calculating a number of days from the beginning of the cycle.

Optionally, the change in the representative temperature value associated with the second time window is determined in part using the representative temperature value associated with the first time window.

Optionally, the representative temperature value for each time window is determined in part using temperature data obtained in both time windows.

In one embodiment, determining whether a temperature change event occurred in any of at least two preceding extended periods comprises determining whether a temperature change event occurred during an extended period 4 or more days prior to the extended period and determining whether a temperature change event occurred during an extended period fewer than 4 days prior to the extended period.

In one embodiment, assessing the variation in the representative temperature value associated with the first or second time window comprises calculating the change in representative temperature value from a previously-determined representative temperature value.

Optionally, determining whether a temperature change event occurred further comprises providing information to the user derived from the determination of the temperature change event.

According to a further aspect, there is provided a method of identifying a temperature change event for a female human user, the method comprising:
receiving temperature data for the female human user for at least four extended periods prior to a latest extended period;
determining at least one representative temperature value for each extended period based on at least the received temperature data for that extended period;
determining a reference temperature value based on at least the first representative temperature value;
assessing the representative temperature values using a first assessment method to determine whether a temperature change event occurred 4 or more days prior to the latest extended period;
assessing the representative temperature values using a second assessment method to determine whether a temperature change event occurred 4 or more days prior to the latest extended period;
wherein the first assessment method comprises determining whether each of the representative temperature values is greater than the preceding representative temperature value by more than a threshold amount;
wherein the second assessment method comprises determining whether each of the representative temperature values exceeds the reference temperature value by a variable threshold, the variable threshold being determined based on the number of extended periods between the extended period at which the reference temperature value was calculated and the extended period for the respective representative temperature value the method further comprising combining the outcome of the first assessment method and the outcome of the second assessment method to determine whether a temperature change event has occurred.

The use of multiple methods to determine whether a temperature change event has occurred at a particular time can provide a more definite assessment of whether the temperature change event can be seen in the data, providing greater certainty to users.

A temperature change event can typically be determined to have occurred if the representative temperature value of the user has changed by more than 0.2 degC, typically between 0.2 degC and 0.5 degC, and preferably at least 0.3 degC from a reference or baseline level. Such a change would typically occur within the 2-3 days leading up to ovulation.

In one embodiment, combining comprises making a determination that a temperature change event has occurred only if both the first assessment method and the second assessment method result in a determination that a temperature change event has occurred.

Optionally, the threshold amount is a constant value.

In one embodiment, the value of the variable threshold increases with the time between the extended period and the extended period at which the reference temperature value was calculated.

Optionally, determining whether a temperature change event has occurred further comprises providing information to the user derived from the determination of the temperature change event.

Optionally, the extended periods comprise consecutive extended periods.

According to a further aspect, there is provided a method of identifying a temperature change event for a female human user, the method comprising:
receiving temperature data for the female human user for at least four separate extended periods prior to a latest extended period;
determining a plurality of representative temperature values for each extended period based on at least the received temperature data for that extended period;
assessing the representative temperature values against a plurality of temperature change event criteria;
allocating a score for each criterion that is met;
combining the allocated scores from each criterion; and
determining whether a temperature change event has occurred based on the combined allocated scores.

The claimed method of analysing data to determine whether a temperature change event has occurred can enable the system to detect a temperature change event earlier (based on data from fewer days) and/or with a greater degree of certainty.

In particular embodiments, the criteria include a plurality of:
whether the representative temperature values have risen by a variable threshold amount above a reference representative temperature value, wherein the variable threshold amount differs based on the number of extended periods since the reference representative temperature value was determined;
whether the representative temperature values have risen by a threshold amount during each of the extended periods;
the number of extended periods since the start of the menstrual cycle for the female human user;
the number of extended periods since the last temperature change event for the female human user;

the maximum temperature value of the temperature data during the extended periods;

the minimum temperature value of the temperature data during the extended periods;

the rate of change of the temperature during an extended period;

the rate of change of the temperature between extended periods;

a measure of the similarity with the temperature profile of the female human user during a previous ovulatory cycle;

a measure of the similarity with an average or typical temperature profile for a plurality of female human users during previous ovulatory cycles;

the degree to which the rise in temperature values secondary data detected in relation to the female human user, for example a change in the level of at least one hormone or a change in temperature determined by a secondary temperature sensor; and secondary data received from the female human user, for example a qualitative or quantitative measure of cervical mucus, a level of a hormone, a temperature value obtained from a secondary, external temperature sensor.

Optionally, the allocated score depends on the degree to which the representative temperature values meet or exceed the criterion.

Optionally, the scores allocated for each criterion differ between criteria. In particular, the more indicative of ovulation a criterion is considered to be, the higher a score may be allocated.

In some embodiments, the allocated score is based on a calculated probability that the representative temperature values meet or exceed the criterion.

The method may further comprise providing further information predicting the timing of a further temperature change event or an ovulation event based on the timing of the determined temperature change event.

Optionally, the further information comprises the estimated timing of a future period of fertility for the female human user According to a further aspect, there is provided a method of analysing data to provide an indication of the timing of a temperature change event during an ovulatory cycle of a female human user, the ovulatory cycle being divided into a plurality of extended periods during which temperature data is collected from the female human user, the method comprising: receiving a plurality of representative temperature values for each extended period, wherein the representative temperature values are determined based on the temperature data collected during each extended period;

receiving a plurality of sets of representative temperature values for a plurality of extended periods in previous ovulatory cycles of the female human user;

analysing the plurality of representative temperature values against the plurality of sets of representative temperature values to determine whether a pattern in the representative temperature values is predictive or indicative of a temperature change event occurring for the female human user.

Hence pattern matching techniques can enable a temperature change event to be detected earlier in the cycle, based on the pattern typically seen in the cycle of a particular female. They can also add greater certainty to an assessment that a temperature change event has occurred in a particular cycle if the pattern of the data matches that of data collected in previous cycles.

Optionally, analysing the plurality of representative temperature values comprises determining whether the gradient of a change in the representative temperature values corresponds to the gradient of a change in the representative temperatures values during each of a plurality of previous cycles.

In one embodiment, corresponding comprises matching the gradient of the change to within a predetermined threshold.

In one embodiment, analysing the plurality of representative temperature values comprises determining whether an observed dip and subsequent rise in the representative temperature values over at least two extended periods corresponds to an observed dip and subsequent rise in the representative temperature values during a plurality of previous cycles.

Optionally, the plurality of extended periods in previous ovulatory cycles comprise extended periods in at least 3, preferably at least 6 previous ovulatory cycles.

The method may further comprise calculating based on the analysis an expected extended period during which the temperature change event is expected to occur in the present cycle.

Optionally, the method further comprises calculating a probability of a temperature change event falling within a particular extended period.

The method may further comprise determining whether the particular extended period falls within the expected extended time period; calculating an adjusted probability that the non-disregarded temperature readings encompass a temperature change event based on the determination; and providing information to the female human based on the adjusted probability.

Optionally, each extended period comprises two representative temperature values.

Apparatus aspects corresponding to each of the method aspects set out above are also provided and preferred features of the method and apparatus aspects, which provide further advantages, are set out in the dependent claims. Aspects may be implemented in combination with each other in particular implementations and preferred features of one aspect may be applied to other aspects.

In particular, one apparatus aspect provides apparatus for analysing temperature data from a female human user, the apparatus comprising:

means for receiving temperature data obtained from the female human user using a temperature sensor;

a memory for storing the received temperature data;

a processor for retrieving the stored temperature data from the memory and for implementing the method of any of the preceding aspects or any of the preferable features set out in the dependent claims;

an interface for outputting to an indication means an indication based on a result generated by the processor.

There is also provided herein a temperature sensing system comprising:

a temperature sensor for deployment in or on the body of a female human user for obtaining a plurality of temperature readings from the female human user;

a memory for storing each of the plurality of temperature readings;

a processor for digitising each of the plurality of temperature readings;

a power supply; and a communications interface for communicating the plurality of digitised temperature readings to a central server.

Optionally, the communications interface comprises a first communications interface connected to the temperature sensor for communicating the plurality of digitised temperature readings to an intermediate device and a second communications interface at the intermediate device for communicating the plurality of digitised temperature readings to the central server. The system may further comprise an intermediate device in communication with the temperature sensor and the central server, the intermediate device comprising an intermediate device memory for storing a plurality of processed temperature readings for communication to the central server.

Optionally, the processor is implemented at the intermediate device.

In one embodiment, the intermediate device memory is arranged to store the plurality of temperature readings received from the temperature sensor and the plurality of digitised temperature readings.

In one embodiment, the memory is arranged to cache a plurality of temperature readings and to upload the cached temperature readings periodically to the intermediate device or central server.

Optionally, the temperature sensor has a resolution of at least 0.03 degC, preferably at least 0.01 degC.

Optionally, the temperature sensor has a linear response at temperatures of greater than 36 degC and less than 38 degC, preferably at temperatures of greater than 35 degC and less than 40 degC.

According to a further aspect, there is provided a method of analysing data to provide an indication of the timing of a temperature change event during an ovulatory cycle of a female human user, the method comprising:
  receiving a first plurality of at least 10 temperature readings obtained from a female human user, the temperature readings being obtained from the user during a first extended period;
  receiving a second plurality of at least 10 temperature readings obtained from a female human user, the temperature readings being obtained from the user during a second extended period;
  wherein each extended period comprises a period of at least 2 hours and less than 14 hours and wherein each extended period is separated from any preceding or subsequent extended period by at least 4 hours, preferably by at least 12 hours;
  making a determination that the first plurality of temperature readings encompasses a temperature change event comprising a change in phase from a neutral or negative temperature change to a positive change in the value of the temperature readings during the first extended period, wherein the determination of the positive change is made only if there is a sustained discernable increase in the value of the temperature readings within the extended period;
  storing an indication that a temperature change event has occurred in the first extended period;
  analysing the second plurality of temperature readings to determine whether the second plurality of temperature readings exhibit an increase in the value of the temperature at greater than a predetermined rate;
outputting an indication based on the timing of the temperature change event determined in the first extended period if the temperature readings of the second extended period exhibit an increase in the value of the temperature at greater than a predetermined rate.

Hence there is provided a method of determining whether a temperature change event detected in a first extended period is sustained within a second, subsequent extended period and therefore whether the original temperature change event was a true temperature change event for the user, upon which the rise in progesterone within the user can be determined and hence indications of the fertility status of the user can be based.

According to a further aspect, there is provided a method of analysing data to provide an indication of the timing of a temperature change event during an ovulatory cycle of a female human user, the method comprising:
  receiving a plurality of at least 10 temperature readings obtained from the female human user during an extended period of at least 2 hours and less than 14 hours when the user is expected to be at rest or asleep;
  filtering the plurality of temperature readings to disregard faulty or irrelevant data;
  determining a probability that the non-disregarded temperature readings encompass a temperature change event, based on matching a pattern in the non-disregarded temperature readings to an expected pattern for a temperature change event.

The present aspect may provide a method of determining within the data of a single extended period whether a temperature change event has occurred for a user.

According to a further aspect, there is provided a method of determining at least one representative temperature value for a female human user, the method comprising:
  receiving at least a first, a second and a third plurality of temperature measurements obtained from a female human user during at least first, second and third respective extended periods, wherein each extended period comprises at least one hour and wherein the start of each extended period is separated by at least 4 hours;
  calculating at least one representative temperature value for the second extended period, wherein the representative temperature value is calculated using:
  at least one first temperature value obtained from a plurality of measurements taken during the first extended period;
  at least one second temperature value obtained from a plurality of measurements taken during the second extended period; and
  at least one third temperature value obtained from a plurality of measurements taken during the third extended period.

Hence a method of determining a more accurate representation of the temperature value for a user during a particular extended period may be provided.

There is also described herein a method of analysing data to provide an indication of the timing of a temperature change event during an ovulatory cycle of a female human user, the method comprising:
  receiving a plurality of temperature readings obtained from the female human user during an extended period when the user is expected to be at rest or asleep;
  filtering the plurality of temperature readings to disregard faulty or irrelevant data;
  determining a probability that the non-disregarded temperature readings encompass a temperature change event, based on matching a pattern in the non-disregarded temperature readings to an expected pattern for a temperature change event;
  retrieving data derived from temperature readings obtained from the user in at least six extended periods during a previous ovulatory cycle;

calculating based on the retrieved data a time period during which the temperature change event is expected to occur in the present cycle;

determining whether the extended period falls within the calculated time period;

calculating an adjusted probability that the non-disregarded temperature readings encompass a temperature change event based on the determination;

providing first information to the female human based on the adjusted probability.

The use of pattern matching techniques to determine the probability of a temperature change event in an extended period together with the use of historic data from previous cycles to increase the accuracy and certainty of any predictions can provide a useful technique for identifying temperature change events in the user with a minimum of data. This can enable faster determination of the timing of a temperature change event while still providing acceptable accuracy for the user.

Optionally, the method further comprises determining a plurality of representative temperature values for the extended period from the non-disregarded temperature readings. The use of representative temperature values as described herein may provide a more accurate representation of the basal body temperature of the user. The representative temperature value may be obtained, as described herein, by calculating an average value, for example using a trimmed mean, mean, median, or modal value or by selecting one or more values from the raw data, for example selecting a value obtained at a particular time, e.g. 1 am, or within a particular time window.

The method may further include allocating the plurality of non-disregarded temperature readings from each extended period into a plurality of time windows for each extended period, wherein each extended period comprises at least two time windows. The method may further comprise determining at least one representative temperature value for each time window of the extended period.

Optionally, the method further comprises receiving temperature readings obtained during a plurality of extended periods within the same ovulatory cycle for the female human user. The method may then include using temperature readings from at least one previous extended period in the determination of the probability that the non-disregarded temperature readings encompass a temperature change event.

Optionally, the retrieved data is based on extended periods occurring during a plurality of previous ovulatory cycles.

Optionally, matching a pattern in the non-disregarded temperature readings comprises determining whether a gradient of an increase in the temperature readings is greater than an expected value over a predetermined period of time.

Matching a pattern in the non-disregarded temperature readings may alternatively or additionally comprise identifying a decrease in the temperature followed by an increase in the temperature readings having a gradient greater than an expected value over a predetermined period of time.

The predetermined period of time is optionally shorter than the length of an extended period. Hence changes in temperature are monitored within an extended period.

In one embodiment, an extended period comprises a single continuous period.

In one embodiment, a 12 hour period comprises not more than one extended period.

Optionally, the temperature readings are obtained using an indwelling thermometer. Optionally, the temperature readings are obtained using a thermometer that is in substantially continuous contact with the female human user throughout the extended period. Optionally, the temperature readings are obtained using an intravaginal thermometer.

The method may further include correcting at least one non-disregarded temperature reading for diurnal temperature variation. This may enable a more accurate comparison of temperature data obtained at different times, in particular of data obtained before and after about 2 am.

The first information may comprise an indication of the timing of an ovulation event for the female human.

The method may further include providing further information predicting the timing of a further temperature change event or a further ovulation event based on the timing of the determined temperature change event.

The further information may comprise the estimated timing of a future period of fertility for the female human user.

Optionally, each time window comprises at least 30 minutes, preferably at least one hour, further preferably 3 or 4 hours.

Optionally, the time windows each have a fixed time length and the number of windows in an extended period depends on the length of the extended period.

According to a further aspect, there is provided a method of determining at least one representative temperature value for a female human user, the method comprising:

receiving at least a first, a second and a third plurality of temperature measurements obtained from a female human user during at least first, second and third respective extended periods, wherein each extended period comprises at least one hour and wherein the start of each extended period is separated by at least 12 hours;

calculating at least one representative temperature value for the second extended period, wherein the representative temperature value is calculated using:

at least one first temperature value obtained from a plurality of measurements taken during the first extended period;

at least one second temperature value obtained from a plurality of measurements taken during the second extended period; and at least one third temperature value obtained from a plurality of measurements taken during the third extended period.

The method enables smoothing of data across several days to provide a more accurate representation of changes in the temperature of the user.

In one embodiment, the representative temperature value for the second extended period comprises an average of the at least one first, at least one second and at least one third temperature values.

Optionally, the average is weighted based on the number of measurements taken during the respective first, second and third extended periods. Hence more weight is given to values obtained from extended periods in which a large number of readings were taken as it is presumed that these values are likely to reflect more accurately the temperature of the user. This may be a loose weighting.

Optionally, the at least one first, second and third values comprise average temperature values for the first, second and third extended periods respectively.

In some embodiments, each extended period is divided into a plurality of time windows and a representative temperature value is obtained for each time window of each extended period.

Optionally, each extended period is divided into a plurality of time windows and wherein the at least one first temperature value, at least one second temperature value and at least one third temperature value comprise readings obtained in corresponding time windows in the respective first, second and third extended periods.

The method may further include weighting the calculation of the representative temperature value based on the number of readings in the first, second and third time windows of the respective extended periods.

The method optionally includes calculating the at least one representative temperature value for the second extended period using a temperature value obtained for at least one extended period prior to the first extended period.

In some embodiments, the method includes calculating the at least one representative temperature value for the second extended period using a temperature value obtained for at least one extended period subsequent to the third extended period. In a particular embodiment, the representative temperature value for the second temperature period is calculated using measurements taken from the preceding two extended periods (preferably extending over the preceding two days) and the following extended period (preferably extending over the following day). Hence a calculation of a representative temperature value for a particular day is delayed by one day. The averaging of temperature values over several days around the day in question can increase the accuracy of the representative temperature value. However, limiting the number of days after the day in question that are used in the calculation can enable more up-to-date temperature change analysis to be performed. This can enable an increase in temperature to be identified more quickly after it has occurred, leading to the possibility that the user can be advised of the temperature change event, and the probability of ovulation occurring, as it happens. This may be particularly beneficial for users whose ovulatory cycles are irregular.

According to a further aspect, there is provided herein a method of obtaining a plurality of readings of the temperature of a female human user, the method comprising:
  determining the temperature of a female human user by
    obtaining a temperature reading periodically over an extended period of at least 4 hours to produce a temperature reading data set
  identifying within the data set valid temperature readings, including
    identifying a first plurality of consecutive temperature readings wherein each of the first plurality of readings is within a predetermined temperature range;
    identifying a second plurality of consecutive temperature readings following the first plurality, wherein each of the second plurality of readings is outside the predetermined temperature range;
  disregarding a predetermined number of readings following the first temperature reading in the first plurality of consecutive temperature readings;
  disregarding a predetermined number of readings prior to the first temperature reading in the second plurality of consecutive temperature readings;
  outputting the non-disregarded temperature readings.

In some embodiments, the temperature readings are obtained at a regular interval. The regular interval may be less than 1 hour, preferably less than 30 minutes, further preferably less than 10 minutes. The regular interval may be greater than 30 seconds, preferably greater than 1 minute.

Optionally, the method may further include determining the time at which each temperature reading is obtained and attaching a time stamp value to each temperature reading.

According to a further aspect, there is provided a method of analysing data to identify a change in the temperature of a first female human user, the method comprising:
  receiving a plurality of temperature readings obtained from the first female human user during extended periods encompassing at least three days;
  analysing the plurality of temperature readings to obtain parameters indicative of a pattern in the readings;
  retrieving stored temperature data sets obtained from one or more female human users over a plurality of ovulatory cycles, wherein the stored temperature data sets each comprise a temperature change event and wherein the stored temperature data sets each have associated parameters indicative of the temperature change event; and
  comparing the parameters indicative of a pattern in the plurality of temperature readings to the parameters indicative of the temperature change event in the stored temperature data sets to determine whether the plurality of temperature readings incorporate a temperature change event.

Optionally, the method further comprises receiving at least a second plurality of temperature readings obtained from the first female human user during a second extended period.

Optionally, the method further comprises receiving at least one further plurality of temperature readings obtained from the first female human user during at least one further extended period.

The parameters may include at least one of:
  the rate of change of the temperature readings between subsequent extended periods
  the cumulative rate of change of the temperature readings between the extended periods over the at least three days
  parameters derived from a frequency transformation analysis
  the sign of the change in temperature readings The method may further include calculating the probability of a temperature change event having occurred based on at least one of:
  the extent to which a match is determined between the parameters associated with the plurality of temperature readings and the parameters associated with the stored temperature data sets;
  the number of extended periods to which the plurality of temperature readings relate;
  the change in the values of the plurality of temperature readings.

Optionally, the stored temperature data sets consist of data sets obtained from the first female human user during previous ovulatory cycles.

Alternatively, or in addition, the stored temperature data sets comprise data sets obtained from a plurality of female human users.

In some embodiments, precedence may be given to data sets obtained from the first female human user during previous ovulatory cycles.

Optionally, the parameters include parameters indicative of a dip followed by a rise in the temperature readings.

According to a further aspect, there is provided a method of determining the level of a hormone in a female human user, the method comprising:

obtaining a first representative temperature reading from a first plurality of temperature measurements taken from a female human user during a first extended period of at least an hour;

obtaining a second representative temperature reading from a second plurality of temperature measurements taken from a female human user during a second extended period of at least an hour;

obtaining at least one further representative temperature reading from a further plurality of temperature measurements taken from a female human user during a further extended period of at least an hour;

wherein the first, second and at least one further temperature reading are arranged over a plurality of days;

the method further comprising:

analysing the first, second and at least one further representative temperature reading to determine characteristics of a change in the temperature of the female human user over the plurality of days;

processing the characteristics of the change in temperature to determine a change in the level of progesterone in the female human user over the plurality of days.

Optionally, the characteristics include at least one of:

an absolute change in temperature over the plurality of days;

a rate of change of the temperature over the plurality of days;

a maximum or minimum temperature during the plurality of days;

a maximum rate of change of the temperature over the plurality of days.

There is also described herein a method of analysing data to provide an indication of the timing of a temperature change event for a female human user, the method comprising:

receiving a plurality of temperature readings obtained from the female human user during at least three extended periods encompassing at least three days;

filtering the plurality of temperature readings to disregard faulty or irrelevant data;

allocating the plurality of non-disregarded temperature readings from each extended period into a plurality of time windows for each extended period, wherein each extended period comprises at least three time windows;

determining a representative temperature value for each time window;

determining a reference temperature value for the user based on the representative temperature values for at least the first extended period;

determining whether the representative temperature values for the respective time windows exhibit a temperature change event, the temperature change event comprising a rise in the temperature value within an extended period or between consecutive extended periods having a gradient greater than a threshold value; and providing first information to the female human based on the determination of the temperature change event.

By splitting temperature data from a single night into at least two time windows, a rise in the basal body temperature can be seen within a night, or between one night and the next if the rise occurs during a time when readings are not being taken.

Optionally, the method further comprises correcting at least one temperature reading for diurnal variation, preferably after the temperature readings have been filtered. This can be particularly helpful in detecting a rise in basal body temperature if it occurs within an overnight extended period since it can enable a more accurate comparison to be made between temperature readings taken early in the night and those taken after 3 am.

Optionally, the first information comprises an indication of the timing of an ovulation event for the female human. The temperature rise event itself is not thought to occur at the point of ovulation, but several days after the beginning of the temperature rise. Ultrasound analysis has indicated that ovulation occurs around 3 days after the beginning of the temperature rise. Therefore, the timing of the ovulation event can be calculated based on the timing of the temperature rise and this information can be communicated to the user, their partner and/or their doctor in time for fertilisation, further testing, or treatment to occur within the same cycle.

The method may also include providing further information predicting the timing of a further temperature change event based on the timing of the determined temperature change event. In particular, the expected timing of the rise in basal body temperature in the next cycle, and potentially in further subsequent cycles, can be calculated. This may be done based on average cycle length data for a plurality of female human users, or may be based on one or more cycles of historic data for the particular user for whom the data is being provided.

Optionally, the second information comprises a time period determined based on the day on which the second temperature change event is expected to occur. The time period may be a range of dates during which the temperature change event may occur.

Optionally, the method may further comprise providing third information based on the prediction of the timing of the second temperature change event. The third information may be the estimated timing of a period of fertility, or preferably a period of maximum fertility for the female human user. The third information may comprise the expected day of the next ovulation event for the user.

Optionally, the method further comprises retrieving stored temperature data sets obtained from one or more female human users over each of a plurality of ovulatory cycles, wherein the stored temperature data sets each comprise a temperature change event and wherein the stored temperature data sets each have associated parameters indicative of the temperature change event. The parameters may include details of how the temperature changes leading up to and during the temperature change event in each data set. In particular, the parameters may include information relating to whether the temperature data exhibits a dip in temperature prior to a temperature rise and details of how quickly and how far the temperature rises during and immediately following the temperature change event.

The method may further include comparing the parameters indicative of a pattern in the plurality of temperature readings to the parameters indicative of the temperature change event in the stored temperature data sets to determine whether the plurality of temperature readings incorporate a temperature change event. Such a method may make the identification of a temperature change event faster and more accurate.

Optionally, the stored temperature data sets comprise data obtained from the female human user. Hence previous data obtained from the same woman can assist in identifying more accurately a temperature change event. In particular, the expected timing of a temperature change event can, in part, be predicted from the length of previous cycles for that particular user. Further, the shape of the temperature curve for a particular user may be characteristic around the time of the temperature change event so the system may be able to anticipate an upcoming temperature change event using pattern matching when the start of the characteristic curve is seen prior to the temperature change event.

Optionally, each extended period comprises at least three, preferably at least four or five windows. More windows enable a larger number of data points within an extended period and an increased ability to detect a temperature change event.

Each window may comprise at least 30 minutes, preferably at least one hour. Optionally, the windows each have a fixed time length and the number of windows in an extended period depends on the length of the extended period. For example, an extended period of 6 hours may include 6 windows.

Apparatus aspects corresponding to the method aspects and each of the preferred features described above may also be provided. In particular, apparatus may be provided with means for implementing each of the method steps provided. In particular, apparatus may further comprise a temperature sensor, in particular an intravaginal temperature probe, which may connected directly to a computer system or network or which may be provided together with a base or docking station for data download and/or recharging of the probe. The temperature sensor In particular, elements in a computer network, such as user terminals, a central server and gateway devices may also be provided independently or in conjunction with each other to implement the methods set out herein.

One particular temperature measurement system comprises a temperature sensor for deployment in or on the body of a female human user for obtaining a series of temperature readings from the female human user; a processor for digitising each of the series of temperature readings; a power supply; and a communications interface for communicating the series of digitised temperature readings to a central server. The communications interface and processor may be provided at the temperature sensor or in an intermediate device with which the temperature sensor communicates, for example a base station or docking station. The temperature sensor or docking station communicates with a central server to upload data and download software as necessary to update the operation of the sensor.

Computer programs, computer program products, computer-readable media and/or logic arranged for implementing any of the methods described above may also be provided.

Embodiments will now be described in more detail with reference to the figures in which:

FIGS. 7a and 7b are schematic illustrations of the operation of the system in two ovulatory cycles according to one embodiment;

Measurements of the basal body temperature of a female human user may be obtained in one embodiment using the apparatus and methods described in WO-A2-2008/029130.

Figure 1:
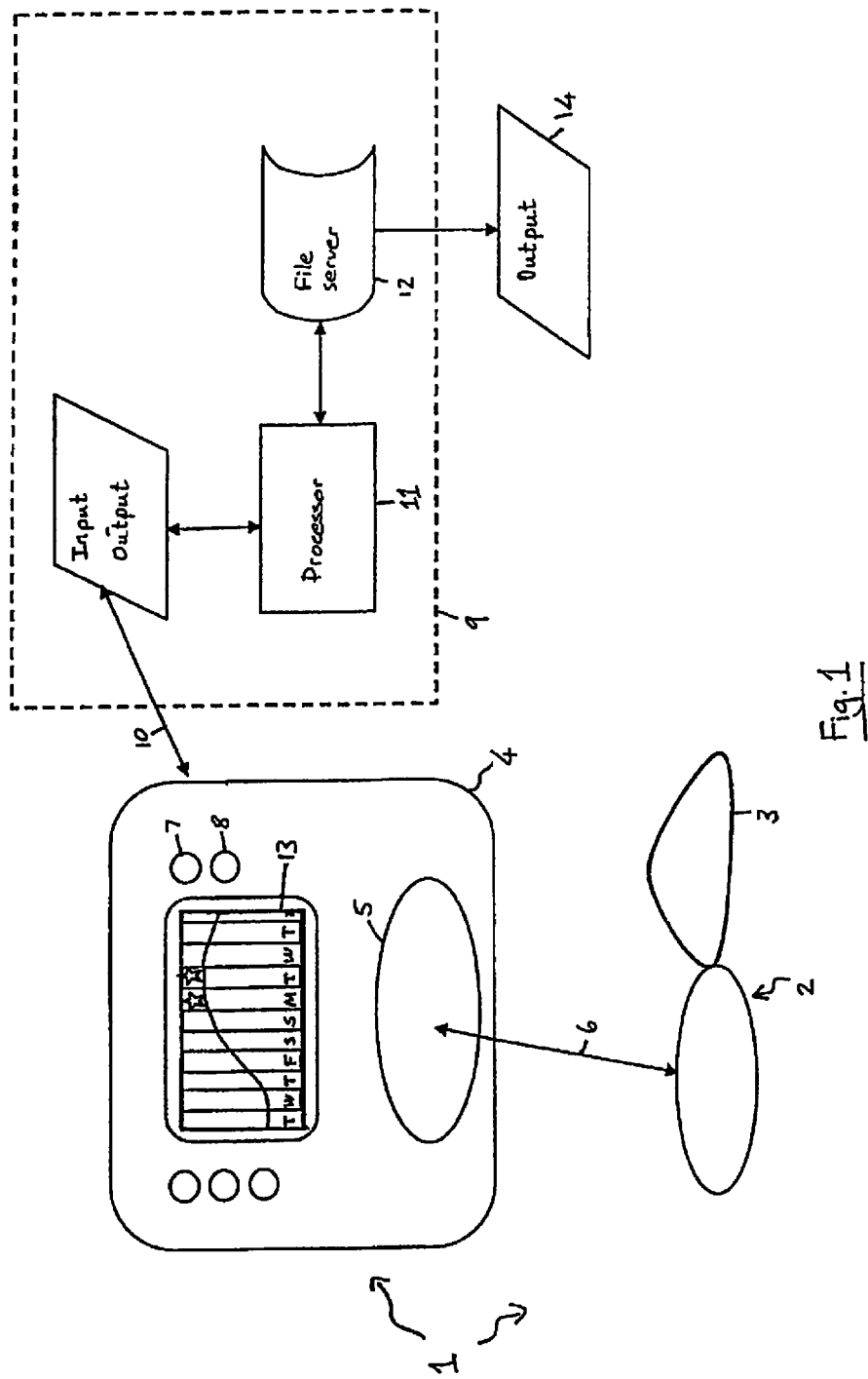
FIG. 1 is a schematic diagram of a device according to one embodiment.

FIG. 1 illustrates schematically an apparatus and method in accordance with a certain preferred embodiment of the invention. It is to be understood that features disclosed in respect of this preferred embodiment may be applied to other embodiments of the invention.

There is provided to a female human a user terminal 1 comprising a temperature measuring device provided in an indwelling unit 2. The indwelling unit 2 is designed for intravaginal use and is smoothly shaped for comfort and hygiene. It is provided with a cord 3 for ease of retrieval. The indwelling device is worn in the vagina every night from the first night following the end of menstruation until such time as the next menstrual period starts. The indwelling unit comprises an electronic temperature measuring means which takes multiple temperatures readings at regular time intervals during the overnight period. The indwelling unit is powered by battery and comprises a memory unit which records the temperature readings taken during the overnight period. The indwelling unit is waterproof and sealed and therefore is either disposed of when the battery is flat, or after a period pre-determined by the system, or else is provided with a rechargeable battery and associated circuitry so that it may be recharged. In one embodiment, the predetermined period of time may be set by the system by setting a number of cycles for which the unit may be used on the reader device or in software associated with the unit, for example in a software application (app) controlling the unit.

When the woman wakes up, she removes the indwelling unit and washes it, by rinsing under a running tap. During the day whilst the woman is awake and active, the indwelling unit of the present embodiment is placed onto a tabletop unit 4 which is also provided to the woman. The tabletop unit is conveniently provided with a recess 5 in its upper surface which is shaped to retain the indwelling unit placed onto it. Both the indwelling unit and the tabletop unit are provided with induction coils which are arranged so that when the indwelling unit is placed in the recess of the tabletop unit the induction coils come into mutual proximity so that the two units may communicate (represented by arrow 6). During the day, the temperature readings stored in the memory of the indwelling unit are transferred to a memory in the tabletop unit. If the indwelling unit is provided with a rechargeable battery, the battery may be recharged by the transfer of electrical energy through the induction coils. At the end of the day the woman removes the indwelling unit from the recess and places it in her vagina so that it may record her body temperatures over the following night.

The skilled person will appreciate that, in other arrangements, the unit may operate in other ways. In particular, the indwelling unit may communicate with the tabletop unit, or base unit in other ways, for example using RFID or BlueTooth communication links or via a physical connection such as by plugging in to an adapter. Alternatively, the base unit may be used only for charging purposes and the indwelling unit may store and process all of its own data or may transfer the data directly to a computer system, for example via a wireless or mobile data connection.

In further embodiments, the indwelling unit may be a standalone device and no base unit may be provided. In such a case, the indwelling unit may perform the necessary data processing steps itself and/or may transmit the data directly to a remote computer system. The remote computer system may be a head-end computer system connected to the unit via the internet. Such a connection may pass through a user's local device, such as a computer, tablet, mobile phone or PDA. In particular, a user application (or "app") may be provided on a user's local device to interface with the indwelling unit, obtain data from the unit and display information and results to the user. In some embodiments, the "app" may communicate with a remote or base computer system to send results or data to the remote computer system. The remote computer system may further provide a web interface for a user where data and results can be displayed and reviewed in more detail.

In some embodiments, the indwelling unit is arranged so that it only records temperature readings during an overnight period. Various methods may be employed to ensure that. In one preferred method the indwelling unit will incorporate a clock and will be programmed to record temperature only during a time period when it is expected that the woman would be asleep. In another preferred embodiment, the woman is instructed that with the exception of brief periods of cleaning after removal and before insertion, the device is to be placed in the recess of the tabletop unit at all times when it is not in the vagina. In such an embodiment the indwelling unit will be arranged to sense whether it is in the recess and programmed to take temperature readings only when it is not in close proximity to the table top unit. It may also be programmed to not record or to disregard temperature readings taken within a short time period (for example, 30 minutes) before and after being placed in the recess of the table top device. Such a short time period will likely contain erroneous temperature readings caused by the indwelling unit being washed or by the thermal lag time when it is first inserted and needs to warm up to body temperature. According to another embodiment, the table top unit is provided with user operated buttons (7, 8) which can be used by the woman to instruct the device that she is about to insert the device or that she has just removed the device.

According to certain preferred embodiments the woman is instructed to press a button (either on the indwelling unit or more preferably on the base unit) to register when she is about to place the indwelling unit and go to bed. Additional input buttons may be provided, for example, for the woman to enter "fever days" to be discounted from calculation or for the woman to signal the start of her cycle (i.e. the first day of menstruation).

When the table top unit 4 has acquired the temperature readings taken the previous night, those readings are automatically transmitted to a remote site (remote site illustrated by dotted line 9, transmission by arrow 10). Transmission may be by wireless telephony or via a telephone line or via the internet or by any other convenient route for which appropriate hardware (for example, modems) and software protocols are provided. According to certain embodiments, transmission need not take place until the woman signals the end of her cycle. A whole cycle's worth of readings may then be transmitted. According to such embodiments, a button may be provided on one of the units (preferably the table top unit) for a woman to signal the end of her cycle and also to start the transmission of data relating to the cycle just completed.

At the remote site there is provided a processor 11 for analysing the temperature readings in accordance with the method of the invention, and a file server 12 for storing the temperature readings and the results of the analysis. The remote site may be in communication with multiple tabletop units being used by different women. The readings from each woman are identified by being labelled by the appropriate desktop unit with a unique identifier code.

Information about the fertility of the woman may be transmitted back to that woman's tabletop unit and displayed on a display screen 13 provided on that unit, said information will also be stored, labelled with the woman's unique identifier code, on the file server.

Information relevant to the fertility of the woman may also be accessed from the file server by other authorised users (represented by output box 14) in possession of the appropriate unique identifier code. Such additional users may include the woman's sexual partner and her physician.

As noted above, the temperature sensor may be provided as an indwelling device, as described above in relation to FIG. 1, or as a sensor that is applied externally to the user, for example as a skin temperature sensor or an aural or oral temperature sensor. The temperature sensor should be able to detect rises in body temperature of between 0.1 and 0.5 degC, typically around 0.3 degC, therefore a resolution of 0.01 degC in the raw data readings is helpful. However, the resolution may be as fine as 0.001 degC and a resolution of 0.003 degC would be typical. The temperature sensor should be linear at least over the range 36-42 degC, preferably over the range 35-42 degC.

Since non-disregarded temperature readings will lie in the range 36-38 degC, measurements to the nearest 0.01 degC within this range will typically be obtained, providing 200 steps for possible readings within that range.

Once obtained, a baseline value (suitably 36 degC) is subtracted from the temperature measurements and the readings are digitised for storage and transmission.

Method of Temperature Data Collection

Multiple temperature readings are taken from the female mammal during an extended period. The extended period may be at least 1 hour long, preferably at least 2 hours long, preferably at least 3 hours long, preferably at least 4 hours long. According to certain preferred embodiment that extended period is between 15 minutes and 6 hours, preferably between 1 to 6 hours, more preferably between 2 and 5 hours, more preferably between 3 and 4 hours. According to certain embodiments the extended time period is an overnight time period or an extended period of rest for the female. One advantage of using an overnight period is that natural fluctuations are reduced due to the constancy of the environment and the relative lack of movement by the female. By "overnight time period" as used above it is intended to mean the period during which the female animal is asleep or expected to be asleep. It will be understood that for certain women (for example those employed to work at night) this time period may in fact take place during the day. Similar considerations apply to the use in nocturnal animals.

During the extended period multiple temperature readings are taken. For example, a reading may be taken every 20 seconds, every minute, or every 5 minutes. Preferably, a reading taken every 1 to 20 minutes, more preferably every 2 to 10 minutes, most preferably every 5 minutes. Preferably multiple temperature readings are taken at regular intervals. Preferably at least 25 temperature readings, more preferably at least 50, more preferable at least 100, more preferably at least 250 temperature readings are taken in the extended period. According to certain embodiments measurements are taken every 5 to 10 minutes over a period of about 5 hours. According to certain preferred embodiments the extended period may extend from shortly before or shortly after the subject goes to bed to 3, 4 or 5 hours later or until the woman wakes up, or for a particular time window during an overnight period, for example, from 1.00 am to 5.00 am or from 12 midnight to 3.00 am. Accordingly, to certain embodiments the time period may be selected to avoid the period after about 3.00 am when a dip in temperature typically occurs, although the Inventors do not report problems with taking readings during this dip.

In some embodiments, the time period may be split into a plurality of time windows, for example 10 am-2 am, and 2 am-6 am. Each time window may be treated as a separate extended period.

In a particular example, the temperature data collection process includes obtaining at least 10 readings in an extended rest period of at least one hour. Preferably readings are taken every 5 minutes for at least 90 minutes which allows a sufficient number of readings to be taken to perform the further analysis in examples described herein whilst also allowing for an initial warm-up period of around half an hour. In preferred examples, at least 20 readings are obtained from the user over a period of at least 2 hours.

The temperature resolution of the sensor in the indwelling unit is preferably at least 0.1° C., further preferably at least 0.05° C. This can enable the expected increase in the basal body temperature of the user to be observed in the data collected.

In another example, as described above, temperature readings may be obtained overnight or for at least a 3 hour rest period and data is collected multiple times each hour, preferably at least 6 times an hour, further preferably 12 times an hour.

Data Filtering

Once the temperature data has been obtained, a step of filtering can be used to identify the data to be used in the further processing steps.

As described in WO-A2-2008/029130, data that is irrelevant and data that is faulty may be disregarded. Irrelevant data includes data that is genuine but irrelevant to the ovulatory cycle. Irrelevant data is genuine data because it genuinely reflects the body temperature of the female. However, it is caused by factors that are irrelevant to the matter of ovulation. It may be produced, for example, by diurnal temperature fluctuations, or by changes in the ambient temperature to which the woman is exposed. Faulty data is data that does not genuinely correspond to the body temperature of the female. It may be produced, for example, by a faulty temperature measuring device or, more likely, by an intrinsic limitation of the temperature measuring device (for example a time-lag in the response of the device to being placed in a body cavity).

Irrelevant or faulty data may arise from a number of sources. For example, data from time period during which the user is experiencing an episode of fever. Also, an indwelling thermometer may be removed or repositioned if it is uncomfortable; it may be removed and washed in either hot or cold water; its temperature may change if the female urinates or if body temperature changes due to changes in the external temperature (caused by changing weather or room heating); changes in clothing or bedding; changes in level of exertion or changes in proximity to external heat sources (for example a hot water bottle or bed partner).

Faulty data is also likely to be generated when the temperature measuring device is first applied to or placed in the subject because of the thermal lag time required for the device to reach body temperature. Irrelevant data may also be produced when the temperature measuring device is not applied to or placed in the subject (for example during periods of non-use which may be intentional or accidental).

A method which allows irrelevant data generated when the device is not in use to be disregarded may have the additional advantage of allowing automatic sensing of the start and end of the extended measuring period. For example if the method involves the overnight use of an indwelling temperature measuring device, said device being stored at room temperature during the day, a step of disregarding irrelevant data will permit the temperature readings generated during the day to be disregarded and assist in the identification of separate extended periods each corresponding to an overnight period. This will remove the need for manually "switching on" the device each night. Faulty or irrelevant data may be identified by applying any suitable characteristic known to be associated with faulty or irrelevant data. Such characteristics include:

1. Temperature readings clearly out of the temperature range found in female mammals of the species in question, for example temperature readings above or below that expected of a 1 female mammal of a particular species. For example more than 2 or 3 or 4 degrees Celsius above or below the expected body temperature of the mammal, for example in the human more than 38° C. or less than 36° C.

2. Temperature readings that whilst they may be within the range expected from female mammals of the species in question are not within the range expected for the individual in question (as determined from historical data previously obtained from that individual, for example temperature readings above or below that expected of an individual female mammal. For example more than 0.5, 0.6, 0.7, 0.8, 0.9 or 1, 2 or 3 or 4 degrees Celsius above or below the expected body temperature of the individual female mammal.

3. Temperature readings which differ from preceding or following values by such a degree as to indicate changes of temperature (heating or cooling) at a rate too high to be expected to be observed in the body temperature of a female mammal. For example heating or cooling rates of more than 0.1° C. per minute, of more than 0.2° C. per minute, of more than 0.3° C. per minute, of more than 0.4° C. per minute, or more than 0.5° C. per minute, or more than 0.6° C. per minute, of more than 0.7° C. per minute, of more than 0.8° C. per minute or of more than 0.9° C. per minute or of more than 1.0° C. per minute may be characteristic of faulty or irrelevant data.

4. Temperature readings which are clearly outliers may be characteristic of faulty or irrelevant data. For example a single reading or relatively few temperature readings differing substantially from the other temperature readings collected during the extended period are unlikely to indicate a true change in temperature but are more likely to be indicative of faulty or irrelevant data.

5. Temperature readings tagged with supplementary data, for example readings tagged by data indicating that the female was suffering from a fever.

6. Temperature readings obtained immediately before or immediately after temperature readings showing any other characteristic of faulty data. For example readings of below 36° C. may be identified as faulty or irrelevant according to characteristic 1 above. The readings obtained 20 minutes before and 20 minutes after such a reading may also be identified as faulty or irrelevant.

Temperature readings having one or more characteristics of faulty data are disregarded, meaning that they are not included in subsequent steps of the method.

Readings which are significantly influenced by diurnal temperature changes may be characteristic of irrelevant data and may, according to certain embodiments be disregarded. For example, if the temperature readings are taken in a human woman during overnight extended periods, the temporary core temperature dip which occurs in humans just before waking may be disregarded according to certain embodiments. Diurnal temperature changes which are unconnected to levels of female hormones and therefore unrelated to ovulation may also be observed in male mammals. Therefore temperature readings taken from female mammals that show similar characteristics to those observed in males of the same species may, optionally be regarded as characteristic of faulty or irrelevant data and be disregarded.

Readings which are identified as raised due to illness by pattern recognition algorithms may be recognised as having one or more characteristics of faulty or irrelevant data and be disregarded.

Readings which occur with the commencement of use, or at the end of use, of the device and which may be attributed to the device reaching a new thermal equilibrium may be recognised as having one or more characteristics of faulty or irrelevant data and be disregarded.

In some embodiments temperature readings may be taken substantially continuously. In such embodiments, the data filtering methods described herein may be used to identify the temperature readings that should be used for further analysis. Hence a large proportion of the temperature readings may be disregarded in such embodiments.

In a particular embodiment, it may be sufficient simply to use any data that falls consistently within a particular temperature range (for example 36° C.-37.5° C.) for a consistent period of longer than 20 minutes. Alternatively, or in addition, the filtering process may detect the first consistent set of data within the temperature range and continue to use the data until a set time (typically 20 to 30 minutes) before it falls below the temperature range.

As an additional check, particularly if the data is associated with a timestamp, the process may further verify whether the particular data falls within the 12 or 24 hour period associated with the extended period in question. This is to ensure that the data is assigned to the relevant extended period.

In an alternative approach, data filtering may be achieved using a pattern matching approach. A predicted pattern of expected temperature readings for an extended period can be generated. This may be done based on theoretical or computer models or based on historical data from previous extended periods. The predicted pattern is preferably adapted and updated as more data is collected, either based on a data collected from all users of the device or based on data collected from the specific user of the device. A further step includes defining which data within the predicted pattern should be retained and used for further analysis. This may be done manually or by automatically excluding data falling within criteria for fault and irrelevant data such as those set out above.

The predicted pattern can then be compared to data collected in further extended periods to identify which data from the further periods should be used in the further processing and analysis steps.

In a further processing step, in order to identify where the system might find a relevant "pattern" in the data, a processor may create a 14 hour "window" in the data centred on a point 4-5 hours prior to download of the data being initiated. It is likely that the data in such a window will include all relevant data for a single extended period. The data in the window can then be analysed to determine whether it incorporates a whole extended period. For example, the data may be assessed to determine whether the whole of an expected data pattern is included in the window. In particular, whether there is a characteristic rise in temperature when the user inserts the device, followed by a relatively stable period of temperature readings, and finally a fall in temperature following removal of the device.

Such an approach may enable the system to omit irrelevant data without further analysis of this data, for example by omitting data obtained during a daytime period.

Once such data has been obtained, based on a pattern matching algorithm or window system as described, the data may be further analysed for faulty or irrelevant data as described above. In particular, in one embodiment, the following filtering steps may be applied:

select only temperature readings that are within a predetermined range (36-37.5° C.).
  omit readings from at least the first 20 mins (warm up time)
  omit readings taken before (for example for a period of 10 mins) and after (for example for a period of 20 mins) any temperature dip (this may occur due the device having been taken out and reinserted)
  omit the readings from at least the last 10 mins (this may be after the device has been removed but while it is cooling down to the ambient temperature)
  adjust for or remove data related to diurnal variation (in particular to adjust for the rise in temperature observed after 2 am)
  remove any data that shows too high a rate of change of temperature.

In some embodiments, the raw data that has been filtered according to the techniques described herein can then be used directly in the analysis of changes in the basal body temperature. However, in many embodiments, further processing of the raw data can be helpful in order to bring out more clearly the pattern of changes in the basal body temperature that are caused by the ovulatory cycle. It may be particularly helpful to determine for each extended period one or more representative temperature readings as will now be described in more detail.

Conversion of Data to a "Representative Temperature Reading"

In order to compare and analyse temperature readings obtained from different extended periods, it can be helpful to obtain one or several representative temperature values for each extended period or to obtain a comparative measurement between selected measurements within extended periods. For example, a comparison is made between single measurement points matched in time from within two or within several extended periods. According to certain preferred embodiments a single representative value is obtained for each extended period. According to other embodiments several representative temperature values are obtained for each extended period. An extended period typically lasts for several hours. Representative temperature values may, for example, be obtained for each hourly or half hourly interval of the extended period.

Preferably within each 24 hour period there is a single extended period and a single representative temperature value is obtained for each extended period. Representative temperature values may, for example, be obtained using any of the following methods:

Calculating the mean of the non-disregarded temperature readings collected during the complete extended period or collected during a specific time interval of the extended period (if more than one representative value is to be obtained for each extended period).

Calculating the median of the non-disregarded temperature readings collected during the complete extended period or collected during a specific time interval of the extended period (if more than one representative value is to be obtained for each extended period).

Calculating the mode (most commonly occurring temperature reading) from the data collected during the complete extended period or collected during a specific time interval of the extended period (if more than one representative value is obtained for each extended period).

Choosing the temperature reading or readings at a particular distance in time from the start or the end of a stretch of non-disregarded temperature readings. For example, the representative value may be chosen as the temperature reading taken halfway through the stretch of non-disregarded temperature readings. Alternatively representative values may be chosen as the temperature readings taken at regular intervals during a stretch of non-disregarded temperature readings, for example, every hour or every half hour.

By the use of deviations of single measurement points from a representative or from an idealised model of diurnal temperature change, for example by calculating a standard deviation, a variance or higher moments.

Calculating a derivative or integral of the temperature readings over time collected during the complete extended period or collected during a specific time interval of the extended period (if more than one representative value is to be obtained for each extended period). For example, the slope representing the rate of change of temperature. According to certain preferred embodiments, all temperature readings that remain after those having one or more characteristics of faulty or irrelevant data are disregarded are used as representative temperature values.

It has been unexpectedly discovered that it is preferable to obtain a representative temperature value that is not influenced, or not significantly influenced, by the maximum or minimum readings for extended period. Examples of such values include the "trimmed mean" of the temperature readings. To obtain such a trimmed mean one disregards a pre-determined number of the lowest and a pre-determined number of the highest readings obtained during an extended period and calculates the mean of those readings that remain. Median and mid-percentile (for example 10th to 90th or the 20th to 80th percentile or the 30th to 70th percentile values are also relatively immune to the effects of other temperature readings and are preferred in accordance with certain embodiments.

It is noted that irrelevant temperature readings are more likely to come about because of heating of the female subject than by cooling of the subject (i.e., a woman's temperature during an overnight (asleep) extended period is more likely to deviate from her true basal body temperature in an upward rather than downward direction). That is to say, a woman is more likely to experience a temporary and irrelevant temperature rise than she is a temporary and irrelevant temperature fall.

This observation means that a better representative temperature value may be obtained for an extended period by use of an algorithm that gives greater statistical weighing to temperature readings that are lower than the median temperature reading than is given to the temperature readings that are higher than the median temperature readings (whilst, of course, at the same time giving little weight to the minimum temperature reading and those readings near to the maximum temperature reading).

It has been found that the 25th percentile of non-disregarded temperature readings makes an especially good representative temperature value for an extended period. Other readings near to the 25th percentile of non-disregarded temperature readings will also serve well. According to certain preferred embodiments the representative temperature value for an extended period is the 10th to 60th percentile value of the non-disregarded temperature readings. More preferably it is the 11* to 50th percentile value, more preferably the 12th to 40th percentile value, more preferably the 13th to 46th percentile value, more preferably the 14th to 44th percentile value, more preferably the 14th to 42nd percentile value, more preferably the 15th to 40th percentile value, more preferably the 16th to 38th percentile value, more preferably the 17th to 37th percentile value, more preferably the 18th to 35th percentile value, more preferably the 19th to 33rd percentile value, more preferably the 20th to 31st percentile value, more preferably the 21st to 29th percentile value, more preferably the 22nd to 28th percentile value, more preferably the 23rd to 27th percentile value, more preferably the 24th to 26th percentile value. Most preferably it is the 25th percentile value.

It will be appreciated that under some circumstances the temperature readings may be subjected to processing which will result in both the disregarding of faulty and irrelevant data and the obtaining of a representative temperature value in a single step or calculation process. For example, if one were to take the raw temperature readings of an extended time period and calculate a trimmed mean one would be disregarding outlying temperature readings (likely to be faulty or irrelevant data) and obtaining a representative temperature value in a single step.

Processing of Data to Smooth Temperature Curve

Once representative temperature readings have been obtained for a particular extended period or time window, these may be subject to further processing to smooth the data between time windows as described below.

In a particular embodiment, a sliding average technique may be used to smooth the data between extended periods. Preferably a sliding window covering 3-5 days is used centred on the day for which the adjustment is being made.

In preferred embodiments, the average is weighted by the number of readings of raw data within the particular time window or extended period.

In a particular embodiment, the adjustment preferably takes into account data from the present extended period together with data obtained in the extended periods covering the preceding and following two days. Hence the basal body temperature data is averaged across a 5 night sliding window (−2 to +2 nights).

As described in more detail below, in this embodiment, the final adjusted value for a representative temperature value for a particular extended period is therefore made two days after the extended period itself. In some embodiments, the unadjusted value can be used in the analysis of temperature changes and can be adjusted daily based on subsequent readings until a final adjusted value is reached 2 days after the extended period.

As also described below, in many methods, the determination of whether a temperature change event indicative of ovulation has occurred relies on the identification of 3 days of consistently raised temperature readings. To fully calculate the representative temperature reading for day n of a cycle, data is required for days n−2, n−1, n, n+1 and n+2. If day n is the first day of a temperature change event, then temperature values for days n+1 and n+2 must be calculated to confirm the temperature change event. However, to calculate the representative temperature value for day n+2, data is required from days n, n+1, n+2, n+3 and n+4. Therefore, the start of the temperature change event on day n can be detected on day n+4. It is understood from a study of ultrasound data that ovulation usually occurs around 3 days after the start of the temperature change event so the method described above can be used to inform the user of ovulation one day after it has occurred.

Alternative methods and data processing techniques can be used to bring this time of prediction forward so that ovulation information can be provided to the user in real time or before the ovulation event, while still maintaining a high accuracy of information.

In a particular embodiment, a 3-day rolling average of data may be sufficient to smooth the temperature readings and maintain sufficient accuracy to detect the temperature change event reliably. While representative temperature values may be used in the 3-day rolling average calculation, more accurate data may be obtained if more than one representative temperature value is used for each extended period (for example a representative temperature value can be calculated for each hour within the extended period) or if the raw temperature reading data is used without generating representative temperature values, preferably with irrelevant and faulty data first being filtered out.

With the use of a 3-day rolling average, a temperature change event occurring on day n could be detected on day n+3 (when the data for calculating the value on day n+2 is available). This would enable the temperature change event to be reported to the user within 3 days of the temperature rise having started, which is likely to be the day of ovulation.

In alternative, but related embodiments, use of a 5 day rolling average taking into account data from 3 days before the day in question to one day after the day in question, that is from day n−3 to day n+1, would also be able to reliably identify a temperature change event 3 days after it started. Hence the user would be informed of probable ovulation on the day of ovulation itself. This may be useful since, once an ovulation event has been detected, the user is aware that they are entering a non-fertile period. The user can then potentially stop using the device until after their next menstruation, which may make the device more convenient for the user since it reduces the number of days in the ovulatory cycle on which the user needs to use the device.

The skilled person will appreciate that the embodiments described above may also be combined to improve the accuracy and speed of the temperature change detection. For example, a 3-day rolling average may be used to obtain a working representative temperature value for the past 2 days. This working representative temperature value may be updated and refined into a final representative temperature value as more data becomes available in subsequent days, for example by recalculating the value to be formed from a 5 day rolling average. In this way, the accuracy of the longer-term representative temperature values can be maintained while obtaining a more up to date prediction of the temperature change and an associated ovulation event.

The skilled person will appreciate that similar methods of smoothing the temperature data may also be employed in other embodiments on the raw data itself, preferably on the filtered raw data. Hence such embodiments may omit the step of calculating a representative temperature reading for an extended period. In such embodiments, the data may be smoothed or averaged using a larger number of data points but preferably still over the 3 or 5 day time windows described above.

Analysis Using Representative Temperature Values

Once the representative temperature values have been determined, and preferably adjusted using weighted mean techniques as described above, the data can then be analysed to determine an indication of the date of ovulation by finding a consistent temperature rise. Two approaches to doing this are described below: the use of thresholds and pattern matching.

While techniques described herein are primarily related to identifying a temperature rise of at least 0.3° C. over a period of 3 days, it is noted that a prediction of sufficient accuracy may be obtained by identifying a temperature rise of 0.2° C. Identification of a temperature rise of 0.2° C. may be used to provide a user with an initial indication of ovulation at an earlier time, but at a lower accuracy level, and this initial indication may be later confirmed at a higher level of accuracy or overturned when further data is available.

Thresholds

As described in WO-A2-2008/029130, in one embodiment, the mean of at least three consecutive representative temperature values is obtained and compared with the following 3 representative consecutive representative temperature values. If the following 3 consecutive temperature values are higher than the mean, ovulation is deemed to have taken place on the corresponding to the first representative temperature value. If not, the analysis is repeated but this time the mean is obtained from 4 consecutive representative temperature values. If ovulation is not detected the analysis is repeated again but this time the mean is obtained from 5 consecutive temperature values, then from 6, 7, 8, 9, 10, etc until ovulation is detected or the end of the cycle is reached.

In order for ovulation to be deemed to have occurred the 3 consecutive representative temperature values should be higher than the mean (the "cumulative mean" described above) by more than a pre-set threshold amount. That threshold amount should be set at a value which provides for reliable detection of genuine ovulations with the minimum of false positives. Preferably the threshold value is from 0.08 to 0.25° C., more preferably from 0.09 to 0.24° C., more preferably from 0.10 to 0.23° C., more preferably from 0.11 to 0.22° C., more preferably from 0.12 to 0.21° C., more preferably from 0.13 to 0.20° C., more preferably from 0.14 to 0.18° C., more preferably from 0.15 to 0.17° C., more preferably from 0.16 to 0.17° C., most preferably 0.1667° C. If, according to the this method, more than one apparent ovulation is detected, further analysis may be used to decide which apparent ovulation is most likely to correspond to the true ovulation. Either the analysis of the representative temperature value may be repeated with an incrementally increased pre-set threshold value (as explained above) until only a single apparent ovulation event is detected, or the timing of the multiple apparent ovulation events is considered and the event occurring nearest to the expected day of ovulation (calculated from data obtained from prior cycles— or if not available from population averages) is chosen as the day of true ovulation.

Preferably, the method used may be further enhanced by using historical data and a Bayesian approach to evaluation or to prediction. 'Prior' (historical) data can be provided either from population data available in the literature or from data available from previously recorded cycle/s for the individual female mammal or preferably from both population data and from the individual female's previous cycle or cycles.

Pattern Matching

In an alternative embodiment, or as a complement to the threshold analysis described above, pattern matching techniques may also be used to identify a consistent rise in temperature commensurate with an ovulation event having occurred.

Pattern matching techniques that may be employed can include:

Fitting a linear slope to the data

Frequency transformation analysis (such as Fourier Transform Techniques) to determine where the temperature change event occurs in the data Matching with patterns of previous cycles, in particular for the same woman Using the marker a "dip" in the temperature readings where this is seen, particularly as a bonus indicator Historical data may also be incorporated into pattern matching techniques (whether this is average or user-specific data) to predict a rise in temperature sooner (for example, by an assessment of whether the time for an ovulatory cycle has passed since the previous temperature change event and an assessment of whether the data is following the usual pattern of temperature rise for the woman in question or the population as a whole)

Output

Following the analysis of data to identify a potential temperature rise in the user, information may be output to the user in several different formats. These may include a prediction of or an indication of the "fertile period" or a window of fertility for the user.

In some embodiments, probabilistic data may be output to the user. This may be an indication of the probability of ovulation occurring on a particular day or the probability of the woman being fertile at a particular time. This may take the form of spot-data, for example "there is a 70% likelihood of ovulation in next 24 hours" or may take a more graphical form, for example a graph of % likelihood of being fertile over the cycle stretching from close to 0% fertility to close to 100% fertility on ovulation day.

In a further embodiment, the device may simply indicate the absence of ovulation in a particular cycle and therefore provide an indication to the user as to whether they are "still" fertile.

User-Adaptive Algorithm

In a particular preferred embodiment, the data analysis algorithms may be user-adaptive. In particular, pattern matching algorithms may be adaptable to enable them to learn characteristics of a particular user's temperature curve, or the temperature "signature" of the user. This may be used to provide an earlier indication of a temperature change event since the algorithm may recognise at an earlier stage the beginning of a temperature change "signature" for the user. Alternatively, or in addition, use of such a user-adaptive system may increase the certainty of the temperature change prediction for a particular day.

Use of Secondary Sensors

In particular embodiments, the temperature readings described herein may be further supplemented or enhanced by the use of secondary sensors, which may be provided in conjunction with the system described herein, either on the indwelling unit itself or in a separate secondary device.

In particular embodiments, the indwelling temperature unit may be implemented in conjunction with one or more of:

a skin temperature sensor or oral sensor—in particular to provide an indication of the body temperature on days when the indwelling sensor is not used one or more accelerometers—these may be used to measure movement of the user, which can enable the body temperature reading to be adjusted for the user's activity level heart/pulse rate monitor—such a monitor may also provide a measure of activity levels of the user luteinizing hormone (LH) test—this may be provided as a sensor or may be an indicator that advises the user when an LH test should be performed. In this case, the temperature sensor data can be used to predict the timing of when an LH test can usefully be performed.

Progesterone/Oestrogen—sensors may be provided to supplement the temperature data since these hormones are also known to follow a cyclical pattern over an ovulatory cycle.

pH sensor—sensors may be provided to supplement the temperature data since pH levels are also known to follow a cyclical pattern over an ovulatory cycle.

impedance sensor—sensors may be provided to supplement the temperature data since impedance is also known to follow a cyclical pattern over an ovulatory cycle.

In particular embodiments, the temperature readings described herein may be further supplemented or enhanced by a measure of a hormone level in the female user. In particular, hormones such as oestrogen, estradiol and progesterone may be monitored. Progesterone may be monitored using a urinary progesterone test. Such measures of a hormone level may be used to increase the reliability of results derived from the temperature change analysis. Alternatively, or in addition, analysis of a hormone level on a particular day can be used as a substitute for the temperature readings, for example if the user forgets or chooses not to use the temperature sensor on a particular night or if the temperature data is found to be unreliable for example due to illness in the user.

In further embodiments, the temperature data may be used to predict and indicate to the user the appropriate timings for further test relating to ovulation. For example, a test for luteinizing hormone (LH) can be helpful in predicting ovulation if it is performed at the correct time in the ovulatory cycle. While LH levels can be monitored using a urine test, accurate testing for this hormone is usually a more complex, expensive and invasive process, requiring blood tests and involvement of trained medical personnel. Therefore, it can be advantageous to use the temperature sensing methods described herein to identify the window of time in which LH levels should be monitored.

Similarly, ultrasound techniques are often used to identify the timing of ovulation in a female. However, to obtain the most accurate information would require the woman to attend a medical centre regularly to obtain an ultrasound image of her ovaries. This is expensive and often impractical. However, the system described herein can be used to help to identify the optimal day on which to employ ultrasound techniques.

Progesterone Monitoring

The temperature monitoring systems and methods described herein can also be used to monitor other aspects of the health of a female human user.

In particular, it has been found that there is a correlation between the basal body temperature and the levels of progesterone in a female human. Hence temperature readings obtained using methods described herein may be used as a proxy to provide an indication of progesterone levels in the user.

In particular, characteristics of the change in basal body temperature may be used to determine levels of hormones such as progesterone. Such characteristics may include an absolute change in the temperature over the plurality of days, a rate of change of the temperature over the plurality of days, a maximum or minimum temperature during the plurality of days and/or a maximum rate of change of the temperature over the plurality of days. For example, an increase in temperature of between 1 and 2% over a 3 day period may indicate a corresponding rise in the levels of progesterone in the body.

It is noted that an increase in progesterone levels in a female human user who is in the very early stages of pregnancy is indicative in some woman of an increased likelihood of miscarriage. Therefore, monitoring the levels of progesterone by applying the temperature measuring techniques described herein may provide a straightforward way to monitor the progression of a pregnancy.

FURTHER EXAMPLES

Figure 2:
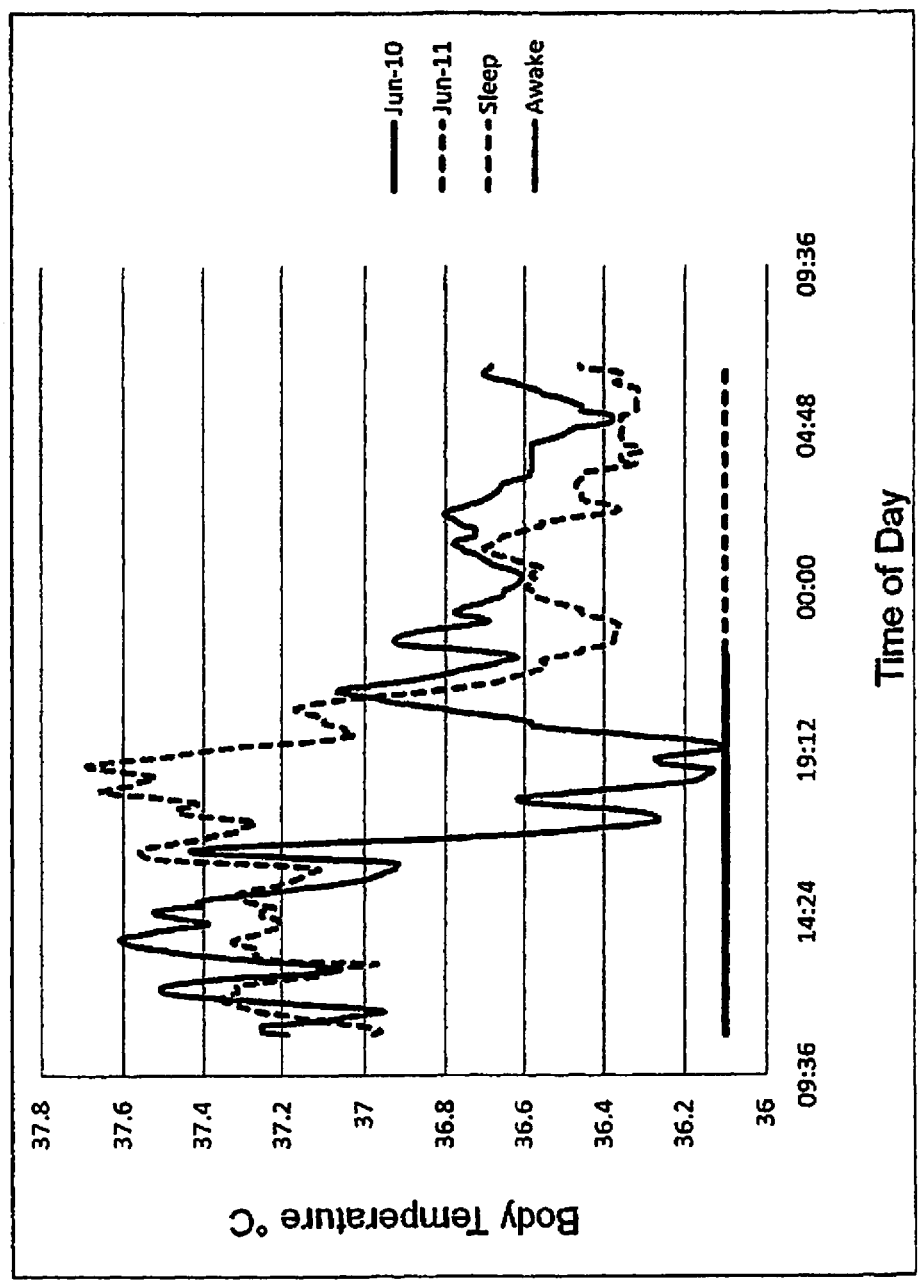
FIG. 2 shows data obtained for an indwelling thermometer worn by a human female for two consecutive days. The x-axis shows the time of day or night and the bar C below the temperature plots shows when the woman was awake or asleep.

FIG. 2 shows temperature readings taken every five minutes using an intravaginal indwelling temperature measuring device from an individual woman over two consecutive days (10 and 11 June). This 48 hour period encompassed both day time periods when the woman was awake and active and overnight periods when the woman was asleep—the bar at the bottom of the graph shows when the woman was awake and when she was asleep. It can be seen from the graph that the overnight temperature readings when the woman was asleep are subject to fewer fluctuations. This is because they are subject to fewer irrelevant temperature changes. This data suggests that it may be preferable to obtain representative temperature values from temperature readings obtained during an overnight time period when the woman is asleep.

The conclusion drawn from FIG. 2 is reinforced by the data shown in the table below which compares the standard deviation (SD) of temperature readings taken every 5 minutes both during the day and during an overnight time period when the subject was asleep. Data is presented for two different women (subject 1 and subject 2) over two 24-hour periods for each woman.

Figure 3:
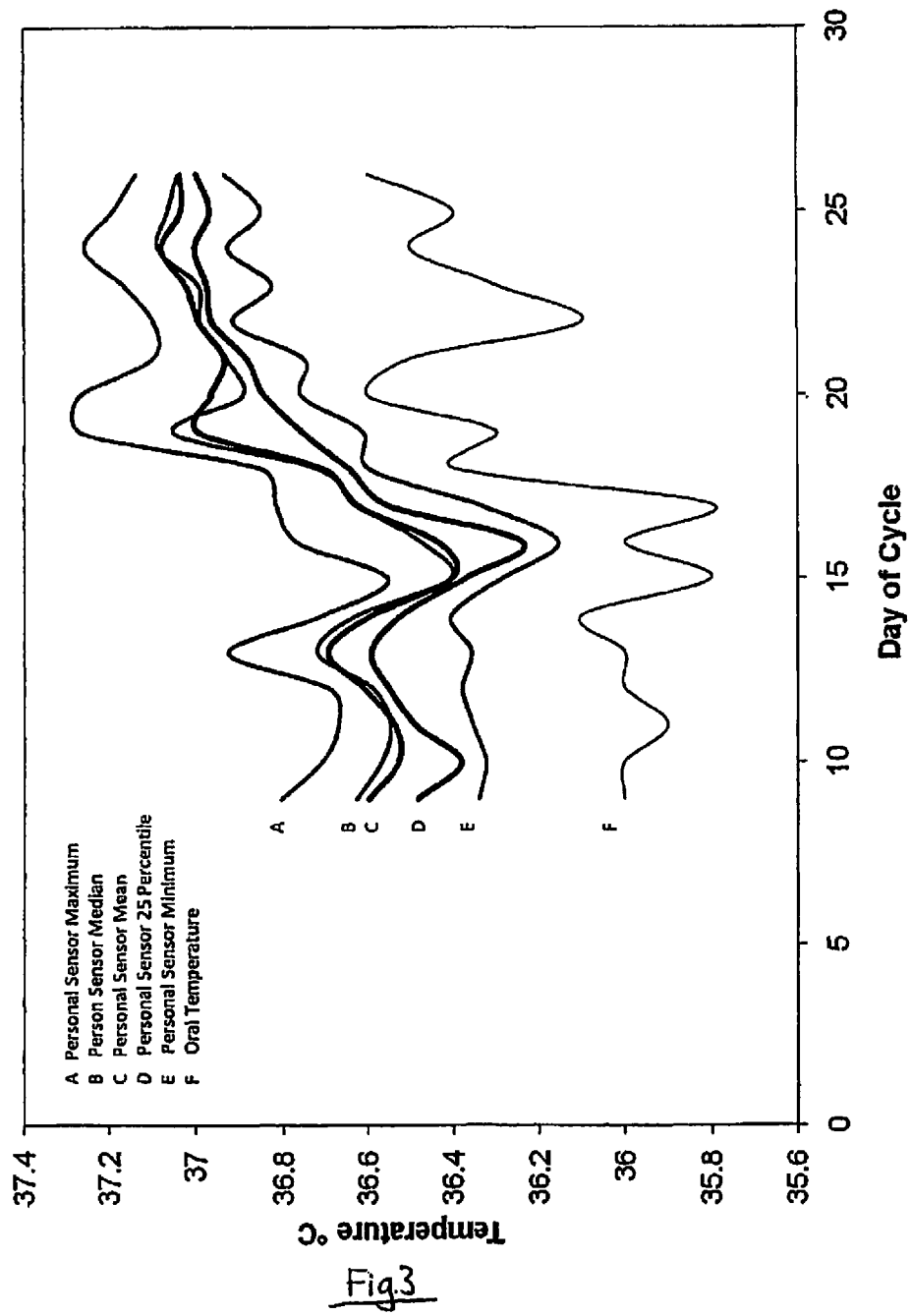
FIG. 3 shows processed data obtained from a woman over her complete ovulatory cycle (except for days 0 to 8 where menstruation took place)

FIG. 3—Comparison of Alternative Representative Temperature Values

Lines A to E of FIG. 3 plot data derived from temperature readings taken every 5 minutes from an indwelling temperature recording device ("personal sensor") placed intravaginally in a woman from day 9 to day 26 of her cycle. In all cases the reading obtained during overnight periods was processed according to the invention to give a single representative temperature value for each day of the cycle.

Line F plots a once-daily oral temperature reading.

The woman from whom the data was derived was of normal fertility and the cycle shown was an ovulatory cycle. One therefore would expect to see first a temperature slight dip and then a temperature rise as the cycle processes.

Line F shows that the oral temperature readings show a great deal of fluctuation which is because of the influence of erroneous or irrelevant data.

Lines A and E show less of such fluctuations and therefore demonstrate the advantages of taking multiple overnight temperature readings using an indwelling device.

Lines A and E are plotted from representative temperature values that are obtained, respectively, from the maximum and minimum temperature readings obtained during each extended period. It can be seen that in comparison to lines B to D, lines A and E show a high degree of unwanted fluctuations and therefore contrary to what is taught in DE 3342251, the use of maximum and minimum temperature readings as representative temperature values has drawbacks and is not to be preferred.

Lines B, C and D show, respectively, representative temperature values obtained from the median, mean and 25 percentile of the temperature readings in each extended period. It can be seen that the mean, median and 25 percentile are all better representative temperature values over the maximum and minimum, and that the 25 percentile (line D) is better than the other representative values plotted in the graph because it shows fewer fluctuations and corresponds most closely to the woman's true core temperature.

Figure 4:
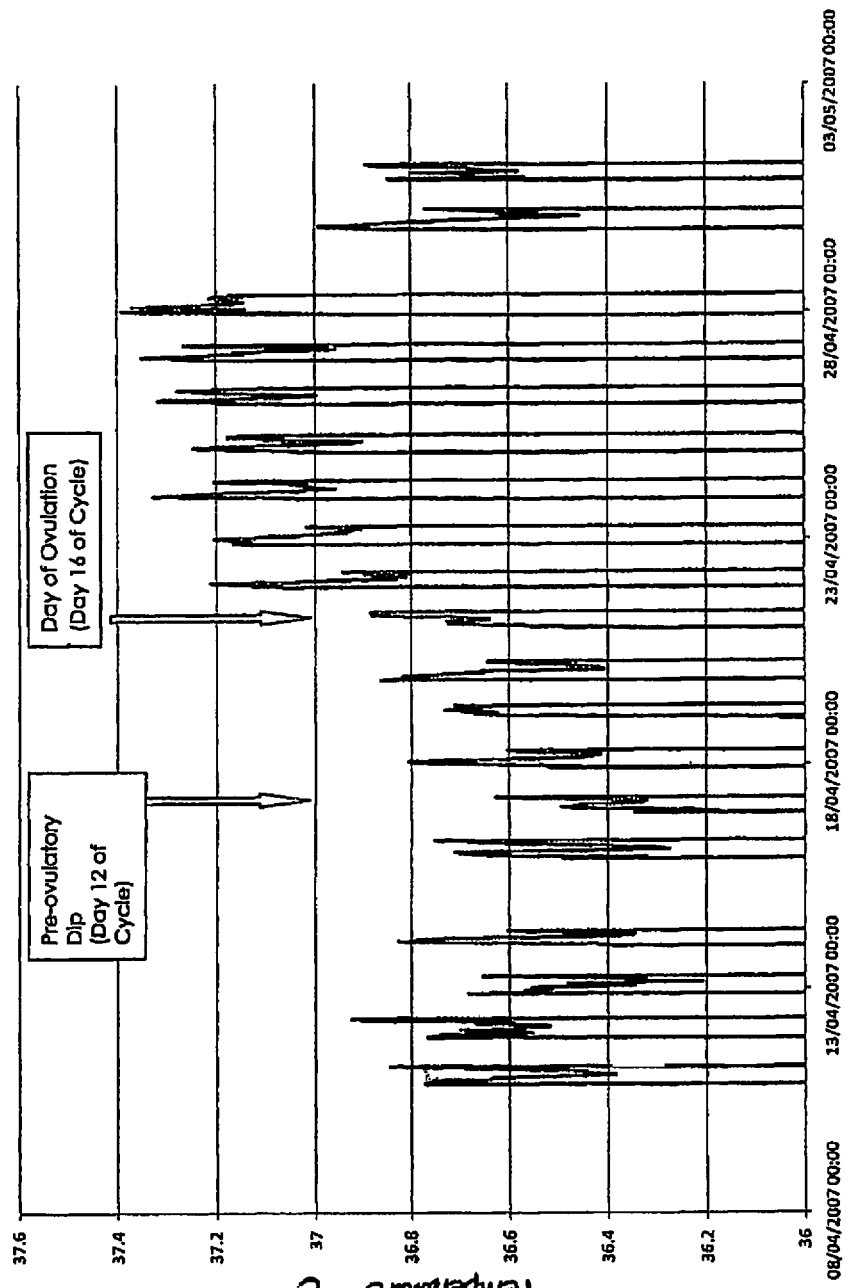
FIG. 4 shows data obtained from a woman over most days in an ovulatory cycle.

FIG. 4 shows temperature readings obtained from a woman during overnight time periods spanning a single ovulatory cycle. Ovulation took place at day 16. The temperature readings plotted demonstrate that the method and device of the invention is sufficiently sensitive to detect not only the LH-associated temperature rise but also the pre-ovulatory temperature dip which is associated with a rise in oestradiol levels.

Figure 5:
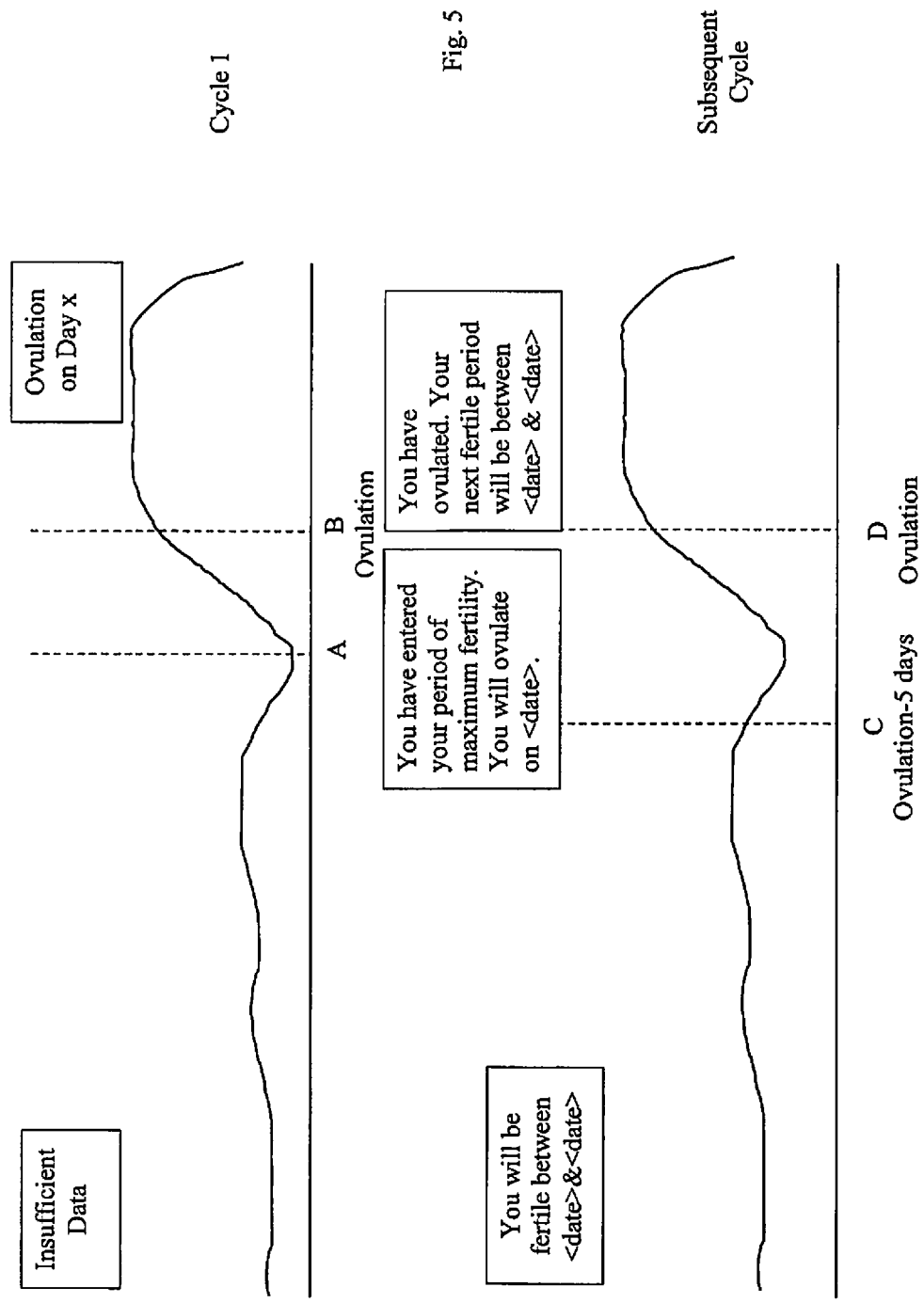
FIG. 5 is a schematic illustration of the operation of the system according to one embodiment.

FIG. 5 illustrates the operation of the system according to one embodiment. During the first cycle of operation, the temperature sensor simply collects data from the user, preferably each night excepting the days of menstruation. A plot of a typical data set for one cycle is illustrated in FIG. 5, although the skilled person will appreciate that the characteristics of the data will vary from user to user and from one cycle to the next.

During the first part of the first cycle, there is insufficient data to make an assessment or prediction of when the user ovulates, although in some embodiments, pattern matching to generic data obtained from a plurality of users may enable some assessment of ovulation dates and fertility to be obtained. During the preliminary period, the apparatus simply informs the user that there is "insufficient data" to predict an expected day of ovulation. However, as the user's basal body temperature rises (Point A in the figure), the system can detect this rise and can determine the day of ovulation for the user (Point B in the figure). The user can be informed of the ovulation date by a message on the apparatus or in associated computer software. If this determination is made in real-time, then adjustments to the timing may be made as data is obtained from subsequent extended periods. Therefore, at the end of the cycle, the system has stored the ovulation date for that user for cycle 1.

The first ovulation date can be used to determine an expected period of fertility in the second and subsequent cycles, based on a cycle length for an average user or, preferably when more data is available, a typical cycle length for the particular user. Therefore, during the first part of subsequent cycles, the device will provide a prediction of the dates of the next fertile period for the user.

At the beginning of the period of maximum fertility, this prediction may change to a message such as "You have entered your period of maximum fertility. You will ovulate on <date>". This period preferably starts around 5 days before the expected date of ovulation for the user.

Assuming the data shows the expected temperature rise around the date of ovulation, the device may then inform the user at the ovulation date "You have now ovulated. Your next fertile period will be between <date>&<date>".

It will be appreciated that the more cycles of data are available, the more accurate the predictions may become.

Also, the date predictions may change during the cycle itself based on the current temperature data being obtained from the user.

It will be appreciated that the data may be displayed to the user on many different devices and in many different forms. In particular, probabilities may be associated with each of the dates mentioned above (for example, there is a 70% chance that you will ovulate on Day X). In other embodiments, the data may be displayed to the user in a more graphical format, for example illustrating the % likelihood of conception or ovulation on any particular day. Alternatively, or in addition, indicator lights may be used, for example on the temperature sensor itself or on a base station, to indicate the fertility (green), infertility (red) or possible fertility (yellow) of the user.

Figure 6:
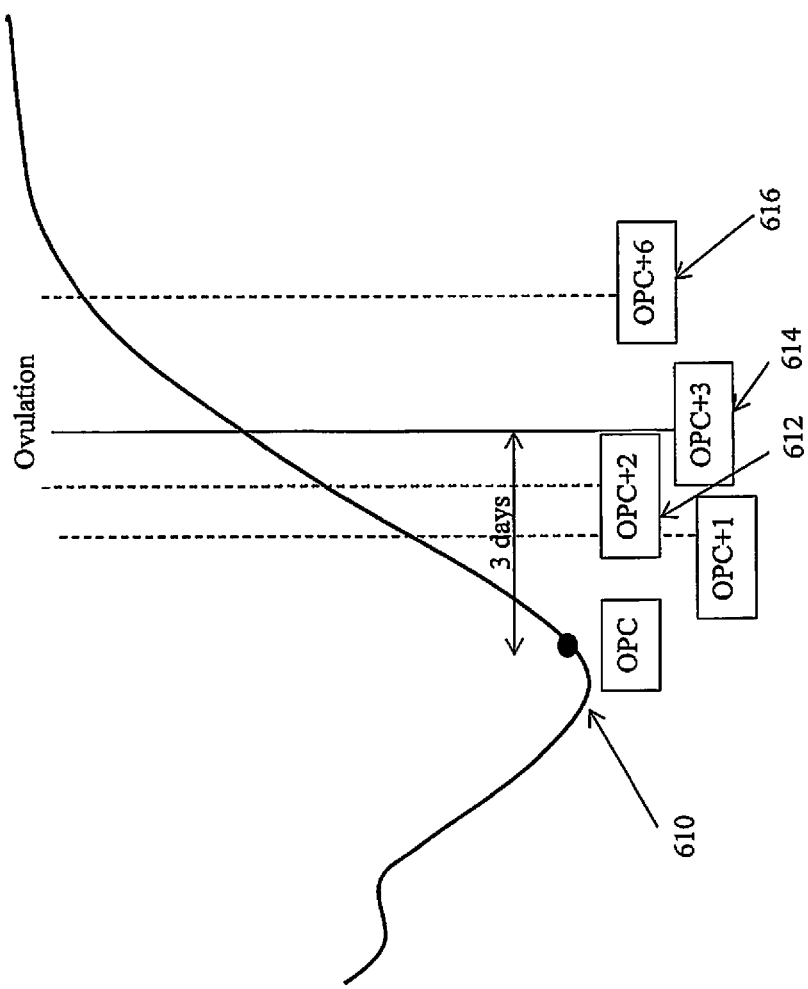
FIG. 6 is a schematic diagram of events within a portion of an ovulatory cycle according to one embodiment.

A method of determining a date of ovulation for a user according to one embodiment will now be described in more detail with reference to FIG. 6, which is a schematic illustration of the variation in temperature for a female human user over a portion of an ovulatory cycle. The skilled person will appreciate that the temperature variation pattern in FIG. 6 is illustrative only and features of the temperature variation have been amplified for emphasis and ease of illustration. Furthermore, while many users will share the key features of the temperature curve shown, there will be variation between users for example in the amplitude and gradient of temperature changes illustrated.

The temperature curve of FIG. 6 is a smoothed best-fit curve using data that has been filtered to remove faulty or irrelevant readings. The raw data would show significant noise and variations in the readings from the smooth curve that is illustrated.

The temperature data illustrated in FIG. 6 shows a characteristic dip 610 in the temperature of the user several days prior to ovulation. The amplitude and number of days over which the temperature dip occurs will vary between users and may not actually appear in the temperature curves of all users. However, around 3 days prior to ovulation, the temperature readings for the user start to rise. The point at which the rise in temperatures begins to occur may be termed the "onset of phase change" or OPC. For the user, the phase is changing from the follicular phase, characterised by a generally lower basal body temperature, to the luteal phase, during which ovulation occurs, which is characterised by basal body temperatures averaging 0.2 degC to 0.7 degC (typically 0.5 degC) higher.

Ovulation occurs for most cycles in most users with a mean centering 3 days after the OPC, and with a Gaussian distribution of results either side of this 3 day mean, indicating that it is a reliable average figure. This can be seen by comparing the day on which OPC is seen in the temperature data to the date of ultrasound scans that show ovulation in the same cycle for the same user. Ultrasound "folliculometry" scans can be used to measure the size of the follicle using a 20 mm cut-off to indicate that ovulation will occur within the next 24 hours. Serial ultrasound scans allow a clinician to establish the pattern and speed of growth of the follicle, and to occur that ovulation has occurred (by being able to see the collapsed previously dominant follicle in an ovary). However, ultrasound scans have the drawback of being spot tests. Hence, unless scans are taken at least once a day on consecutive days and a dominant follicle is observed prior to collapse and the next day after collapse it is impossible to establish the date of ovulation.

In the present system, the OPC is determined based on the temperature data obtained from the user by identifying a meaningful temperature rise within the data over consecutive extended periods. When a temperature rise, in particular a temperature rise having a gradient above a threshold level, is detected, the system determines whether this rise is likely to be associated with an ovulation event by determining whether the temperature rise is sustained over the following days. In particular, as described in more detail below, at least one, and preferably two or more, representative temperature values are obtained over each of at least two extended periods following OPC to confirm that the temperature of the user continues to rise. In more detail, in order to determine reliably the temperature profile of a user in a particular embodiment, each extended period is divided into two windows. These may be windows of time within each extended period, for example 11 pm to 3 am and 3 am to 6 am, or may be formed by dividing the available filtered data into equal portions. For example, if reliable data was obtained only from 12 midnight to 5 am one night, then this data could be split into equal portions. Therefore, based on the filtering and averaging methods described above, two representative temperature values can be obtained for each extended period.

These representative temperature values are then used to monitor how the temperature of the user changes over successive extended periods. In particular, a 5 point average of the representative temperature values can be used to determine a measure of the temperature during a particular time window of an extended period. The average is preferably weighted according to how many non-disregarded temperature measurements are obtained during each time window. This weighting enables more influence to be given to representative temperature values that are based on a larger number of raw data readings. The 5 point weighted average for the first time window of the extended period uses the two representative temperature values calculated for the current extended period, the two representative temperature values calculated for the previous extended period and one of the representative temperature values (preferably the first) calculated for the following extended period. Therefore, it is noted that the final 5 point weighted average value for the temperature during a particular time window of an extended period is not determined until data is available from the following extended period. Similarly, for the second time window of the extended period, a 5 point average is determined based on one representative value from the previous extended period, the two from the current extended period and one from the following extended period. Therefore, for each extended period having two time windows, two average values are determined. It is the change in these average values that is then monitored by the system to identify the onset of an ovulation event, as described in more detail below.

The change in the weighted average is periodically assessed, optionally at least once every extended period, preferably each time a new average is determined, to determine whether the data collected indicates that the onset of ovulation has occurred within the preceding few days. An embodiment of this process is described in more detail below in which three calculations work in parallel on the data to determine whether an OPC event has occurred 6 days, 3 days or 2 days ago. The calculations continue to be performed until one of these events triggers within the cycle.

A first calculation determines whether the system can identify in the current data the occurrence of an OPC event 6 days ago (OPC+6). If the current data is 6 days from the OPC event, then enough data should have been gathered over the preceding days, particularly the days since the OPC event, to identify fairly reliably within the data a sustained temperature rise that started 6 days ago.

In particular, the system assesses how the temperature average has moved over the past 6 days to determine whether there was an increase in temperature 6 days ago that has been sustained over the past 6 days. This assessment of the temperature can be made in two ways; first by assessing the temperature on each day against a reference temperature and second by determining whether the temperature rise is above a predetermined threshold each time the average moves. In the present embodiment, these two assessments are combined to determine whether an OPC event occurred 6 days ago. The use of the combination of the two assessment methods provides a greater degree of certainty with regard to whether the OPC event has occurred than would be provided by one of these calculations alone.

In the first test, a reference temperature is determined for the user from data obtained over a number of days prior to the 6 days currently under assessment. This reference temperature is the average temperature for the user during her follicular phase, prior to the OPC and the change to the luteal phase. The moving average of the temperature is assessed against this reference temperature for each of the time windows in the preceding 6 days to determine whether the average remains consistently above the reference temperature by a predetermined threshold. This ensures that the temperature of the user is remaining consistently high throughout the 6 day period. The predetermined threshold may be arranged to increase over the 6 day period, for example the threshold may rise daily or may be a lower threshold for the first 2-3 days and a higher threshold for the last 3-4 days. By the $6^{th}$ day, the threshold may be at least 0.2 degC, preferably at least 0.3 degC.

In the second test, the assessment of the average determines by how much the average is moving on a day to day (or time-window to time-window) basis. For example, the average calculated from the first time window of the extended period can be compared to the average from the first time window of the preceding extended period, or to the previously-calculated average, to determine whether each movement of the average meets a threshold value, for example at least 0.05 degC The threshold values used may change on a daily basis for each of the preceding 6 days. For example, the threshold may be larger for the first 2-3 days, when the more significant rise in temperature might be expected, and may be smaller for the final 3-4 days, when the temperature is expected to stabilise at a high level.

Preferably, the moving average is assessed against both the reference and moving thresholds and a determination is made as to whether the data from the preceding 6 days meets these criteria.

A probability that the data meets each of the criteria may be calculated depending on how well the data meets the thresholds and these probabilities can then be combined to determine a probability that an OPC+6 event has been detected in the data.

Alternatively, a binary assessment of whether the data fits each of the reference criterion and the moving thresholds criterion and an assessment of OPC+6 can be made if one or both of the criteria are met.

The use of two criteria in this way can increase the confidence in the assessment of whether the data indicates an OPC+6 event, in particular because the two criteria indicate different things about the shape of the data, both of which are helpful in identifying an OPC+6 event. The use of the two methods of assessing the data can be particularly useful with this temperature data since it is likely to include a large amount of noise and non-significant variations.

If an OPC+6 event is determined to have occurred, then the system determines that OPC occurred 6 days ago and ovulation occurred in the female 3 days after the OPC event. The system can then inform the user that she has ovulated and, optionally, give an indication of her date of ovulation. The user can then stop using the temperature sensor until after her next menstruation, at the start of the next ovulatory cycle.

If the OPC+6 conditions are not satisfied, this event does not trigger and the system goes on to make a further assessment of the data to see if it can determine where the user is in her ovulatory cycle, as described below.

If OPC+6 is not triggered, the system proceeds to determine whether an OPC event occurred 3 days ago, by making an OPC+3 assessment. The OPC+3 assessment is made in a different way to the OPC+6 determination. In particular, the data is assessed against each of a number of criteria and a score is determined for each criterion according to how closely the data meets the criterion. These scores are then combined to enable the system to make an assessment of whether an OPC+3 event can be triggered. It is noted that, since ovulation can be deemed to occur 3 days after an OPC event, triggering OPC+3 in the data can enable the system to inform the user that ovulation is occurring on that day.

Criteria that may be included in the assessment of whether an OPC+3 event has occurred include:

whether the representative temperature values (moving average) have risen by a variable threshold amount above a reference representative temperature value, wherein the variable threshold amount differs based on the number of extended periods since the reference representative temperature value was determined. That is, the threshold increases for each day beyond the time at which the temperature started to rise above the reference level. The reference level is an average temperature value determined for the female during her follicular phase, or during the 3-8 days preceding the day on which OPC is assumed to have occurred (the days prior to 3 days prior to OPC+3). This is one of the more indicative criteria, so is preferably allocated a larger number of points in the scoring system.

whether the moving average has moved by more than a threshold amount over each of the past 3-6 movements of the average (that is, whether the representative temperature values have risen by a threshold amount during each of the extended periods). In this case, the threshold value may be constant. This is another indicative criterion, so also has a larger number of allocated points in the present embodiment.

in some embodiments, points may be awarded in the scoring system if the data from the previous day indicated, or came close to indicating, an OPC+2 event, as described in more detail below. Alternatively, the calculation of OPC+2 and OPC+3 events may be kept independent to reduce the risk of one false negative influencing the triggering of another.

the timing within the female's ovulatory cycle, in particular the number of days since the start of the present cycle.

the number of days since her last known ovulation event, or last detected temperature change event for the user.

a comparison with data from previous ovulatory cycles from the same user or from other users (in particular a measure of the similarity with the temperature profile of the female human user during a previous ovulatory cycle or a measure of the similarity with an average or typical temperature profile for a plurality of female human users during previous ovulatory cycles).

the maximum temperature value of the temperature data during the extended periods;

the minimum temperature value of the temperature data during the extended periods;

the rate of change of the temperature during an extended period;

the rate of change of the temperature between extended periods;

the degree to which the rise in temperature values varies from one representative temperature value to the next;

secondary data detected in relation to the female human user, for example a change in the level of at least one hormone or a change in temperature determined by a secondary temperature sensor;

secondary data received from the female human user, for example a qualitative or quantitative measure of cervical mucus, a level of a hormone, a temperature value obtained from a secondary, external temperature sensor.

Different scores are preferably allocated to different criteria depending on how difficult each criterion is to meet and how indicative the criterion is of an ovulatory event.

If the OPC+3 event does not trigger based on the data from a particular extended period, the system goes on to determine whether the data reflects an OPC+2 event, that is whether the data is indicative of an OPC event having occurred 2 days ago.

OPC+2 is calculated in a similar way to OPC+3, in particular with regard to using a scoring system dependent on whether the data meets a number of criteria. If an OPC+2 event is triggered, it is determined that OPC occurred 2 days ago, therefore the system can predict, and inform the user, that ovulation is likely to happen on the following day. Since the OPC+2 analysis is based on fewer days of information than OPC+3, the pattern in this data is less likely to indicate clearly an OPC event and the data is less likely to meet the trigger conditions. In some cycles, it is possible that OPC+2 will not trigger, for example due to there being too much noise in the data obscuring the actual events, but OPC+3 may still trigger on the following day.

It is also noted that, due to the use of the 5-day moving average, the OPC+2 assessment is using data from the 4 preceding days (OPC−1 to OPC+2) to determine whether the moving average has moved sufficiently over the past 2 days to justify a determination that an OPC event occurred 2 days ago. A value for the moving average on OPC+2 cannot be calculated until data is available from the following day, OPC+3.

If an OPC+2 event is triggered on a particular day, then the data generated on the following day is analysed to determine whether it meets the OPC+3 criteria. If so, then this can confirm the date of the OPC event (and hence the date of ovulation). If OPC+3 is not triggered on the following day, then the data from each consecutive day continues to be analysed until OPC+3 or OPC+6 triggers or until the user indicates that she has reached the end of her ovulatory cycle. During this time, the indication shown to the user may be "You are in your ovulatory window" or similar, since it is likely that an ovulation event is occurring at some time around this period if OPC+2 triggered. In particular, if OPC+2 triggered, but OPC+3 does not trigger until 2 days later, this pushes the timing of the OPC event (and hence the ovulation date) predicted by the OPC+2 trigger back a day.

As described above, the system uses these multiple methods and assessment points in parallel. When one first triggers, an ovulation date is set according to the date of the trigger. For example, if OPC+2 triggers on $17^{th}$ January, the system will set the ovulation date as $18^{th}$ January. If OPC+3 triggers on $18^{th}$ January, then this confirms the date, but it may not trigger in which case the date is reset at the next point a trigger occurs.

However, in some cycles, or for some users, none of the algorithm methods OPC+2, OPC+3 and OPC+6 will show a temperature rise with a sufficient gradient to indicate ovulation is going to or has occurred. If the gradient of the temperature rise is still not sufficient to identify an ovulation event at OPC+6, then the system requires the user to continue use of the thermometer until the start of the next menstruation at which point the user indicates that menstruation has started and the system makes an assessment that the user has not ovulated during that cycle and may indicate to the user that the cycle was anovulatory. If such "anovulation" occurs in more than 2 out of 3 cycles, this indicates a requirement for further discussion with a clinician.

Figure 7B:
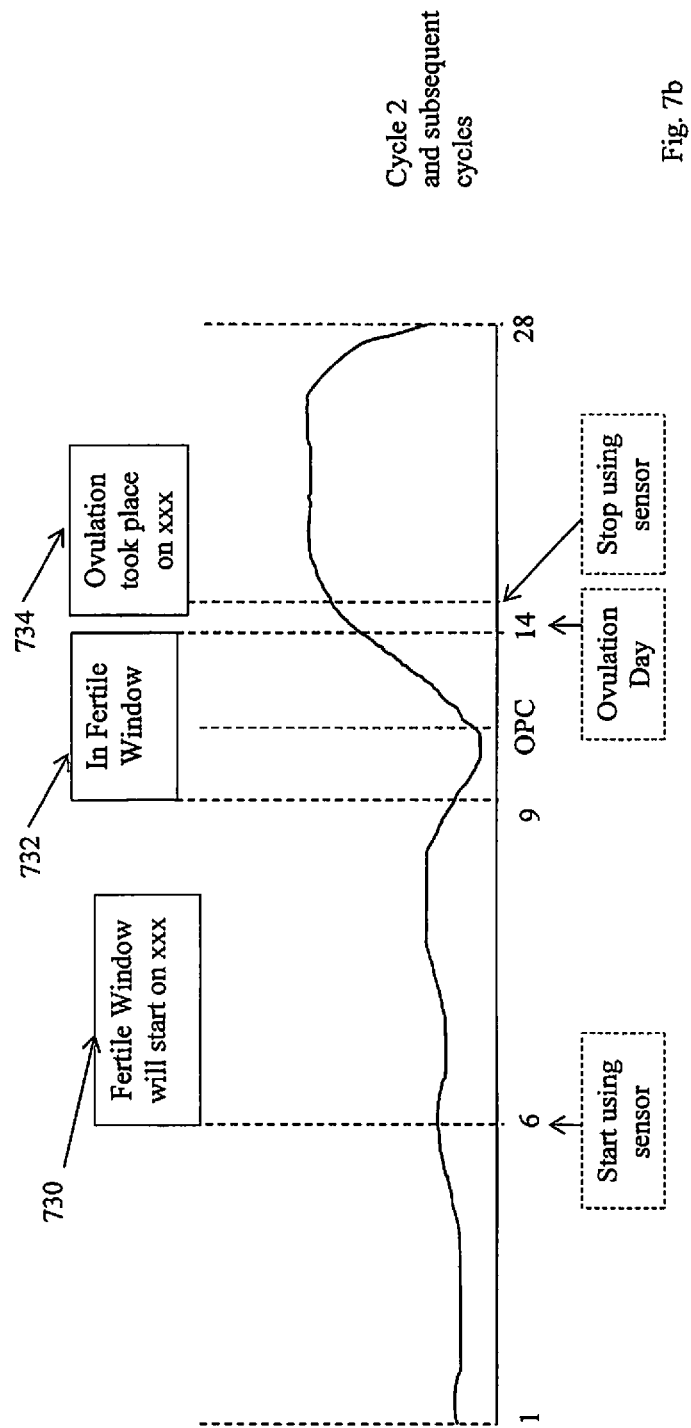

FIGS. 7a and 7b illustrate schematically two cycles of data obtained from a particular user.

FIG. 7a is the first cycle for which the user has used the device. The user starts to use the device at the end of her menstruation period 710 on day 6 of her cycle. The sensor records the temperature at multiple points during one extended period each day (preferably overnight while the user is asleep, as described above). One or more, preferably two, representative temperature values may be obtained from the filtered data for each extended period, in accordance with one of a method described above.

For the first few days of the cycle, variations in the temperature may be observed, but none of the OPC+2, OPC+3 or OPC+6 events is triggered. The output displayed to the user by the sensor device or a base station or computer application associated with the sensor device during this time is "Insufficient Data" 712 or "Insufficient Data. Keep Using the Sensor" or similar. At day 11 of the cycle illustrated in FIG. 7a, the temperature starts to rise. This day is marked as OPC in FIG. 7a, since it is the day on which the onset of phase change occurs from the follicular to the luteal phase which starts with a sustained temperature rise associated with an ovulation event.

The OPC temperature event is followed by a sustained rise in temperature as seen in FIG. 7a. The temperature curve shows the expected gradient for one user for the pre-ovulatory period. The OPC+2 event triggers at day 13, the user is advised that they are entering the ovulation window and ovulation is expected on the following day 714, in accordance with the methods described above. This can be determined by assessing that the change in the moving average of the temperature at day OPC+2 (day 13 in this case) has been large enough over the preceding days to trigger the OPC+2 event as described above and therefore ovulation is likely three days after the OPC event at OPC+3.

Assuming ovulation is predicted in the present cycle by the triggering of an OPC+2 or OPC+3 event, as described above, the device indicates to the user during days 14 to 16 that the user is "In Ovulation Window" 716, since ovulation is predicted to be occurring at some point during this window. In the first cycle in which data is collected for the user, it is difficult for the system to be more precise about the exact day on which ovulation occurs. Therefore, the information is presented to the user as an ovulation window, rather than information relating to an exact day of likely ovulation, in this first cycle.

On day 17, the user output is changed to "Ovulation took place on xxx" 718 or "Ovulation has occurred", since sufficient data has then been collected to identify the OPC event with a greater degree of certainty and the user then knows they can stop using the sensor until they enter the next cycle.

If no ovulation event is determined to have occurred within the present cycle, the user may continue to use the device to collect temperature data until the beginning of their menstrual period. At the start of menses, the user inputs "new cycle" into the device, its associated reader, or software associated with the device, and stops using the device until menses is complete. If no ovulation event is determined to have occurred in the previous cycle, the user is informed by the device that the previous cycle was anovulatory.

FIG. 7*b* illustrates schematically data from the next, or a subsequent, cycle of the same user. The temperature profile illustrated in FIG. 7*b* is very similar to that of the previous cycle, illustrated in FIG. 7*a*, but it is noted that, even for a particular user, the temperature data obtained for different cycles may be quite different. However, most ovulatory cycles will show the features of the OPC followed by a sustained rise in temperature over a number of days.

Again, the user starts using the device on day 6, following the end of their menstrual period. The device now provides an indication of when the user's fertile period or window is likely to start 730. This is based on data obtained from the last cycle; in particular the time from the start of the cycle to the detected ovulation date during the previous cycle.

In particular, the user will be fertile several days prior to ovulation (in most cases, around 5 days), so at 5 days prior to the expected ovulation day, the user is informed that they are in their fertile window 732. This indication continues to be displayed throughout the user's fertile period until an ovulation event is detected in the current cycle, which will mark the end of the fertile period.

As in the cycle described above in relation to FIG. 7*a*, an OPC event is detected in the cycle of FIG. 7*b* (due to the triggering of an OPC+2. OPC+3 or OPC+6 condition) and t the day of ovulation in the current cycle (3 days after OPC) can be detected and recorded. Once ovulation has been detected, the device advises the user of the date of ovulation 734 and the user can stop using the device until their next cycle.

Figure 8:
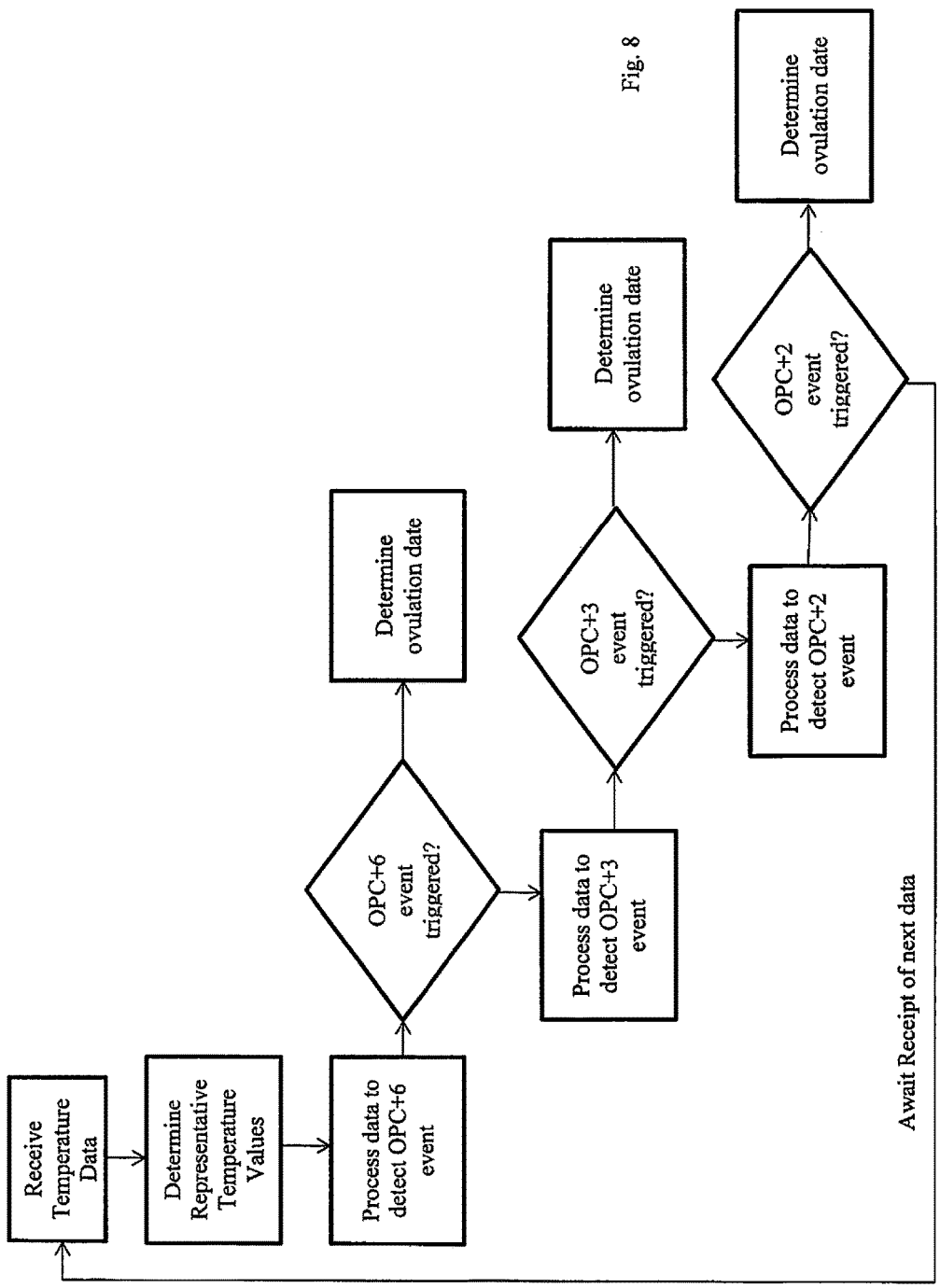
FIG. 8 illustrates a method of processing data according to one embodiment.

FIG. 8 illustrates a method of processing data according to one embodiment. In particular, each time new temperature data is received and new representative temperature values determined, the data is processed in order to determine whether an OPC+6 event can be detected in the data. If so, an ovulation date is determined based on the assessment. If not, the same data is processed to determine whether an OPC event occurred 3 days ago and an ovulation date is determined if OPC+3 is triggered. If not, the same data is processed to determine whether an OPC+2 event is triggered by the OPC event being detected 2 days ago, If so, the date of ovulation is determined. If not, the system awaits the receipt of further data from the next time window or the next extended period in order to repeat the assessments.

The skilled person will appreciate that many variations may be provided to the systems and methods described above within the scope of the claims filed herewith. The description and drawings provided herewith are intended simply to illustrate the methods claims and are not intended to be limiting in any way.

The invention claimed is:

1. An apparatus for determining at least one representative temperature value for a female human user for an extended period, the apparatus comprising:
   a temperature sensor for obtaining a first, a second and a third plurality of temperature measurements from a human user during at least first, second and third respective extended periods;
   a communications interface for receiving at least the first, the second and the third plurality of temperature measurements obtained from a female human user;
   wherein each extended period comprises at least one hour and wherein the start of an extended period is separated by at least 8 hours from the beginning of a subsequent and a preceding extended period;
   a processor arranged to calculate, based on the temperature measurements, at least one representative temperature value for the second extended period, wherein the representative temperature value is calculated using:
      at least one first temperature value obtained from a plurality of measurements taken during the first extended period;
      at least one second temperature value obtained from a plurality of measurements taken during the second extended period; and
      at least one third temperature value obtained from a plurality of measurements taken during the third extended period; and
   a memory arranged to store the representative temperature value for further analysis.

2. A method of determining at least one representative temperature value for a female human user for an extended period, the method comprising:
   receiving at least a first, a second and a third plurality of temperature measurements obtained from a temperature sensor for obtaining a first, a second, and a third plurality of temperature measurements from a female human user during at least first, second and third respective extended periods, wherein each extended period comprises at least one hour and wherein the start of each extended period is separated by at least 8 hours from the beginning of a subsequent and a preceding extended period;
   receiving, via a communications interface, at least the first, the second, and the third plurality of temperature measurements obtained from a female human user;
   calculating, using a processor arranged to calculate based on the temperature measurements, at least one representative temperature value for the second extended period, wherein the representative temperature value is calculated using:
      at least one first temperature value obtained from a plurality of measurements taken during the first extended period;
      at least one second temperature value obtained from a plurality of measurements taken during the second extended period; and
      at least one third temperature value obtained from a plurality of measurements taken during the third extended period; and
   storing the representative temperature value in a memory for further analysis.

3. The method according to claim 2 wherein each extended period comprises at least two time windows and wherein a representative temperature value is calculated for each time window.

4. The method according to claim 2 wherein the representative temperature value for the second extended period is based on at least two temperature values obtained from temperature measurements taken during the first extended period and at least one temperature value obtained from temperature measurements taken during the third extended period.

5. The method according to claim 2 wherein a second representative temperature value for the second extended period is based on at least one temperature value obtained from temperature measurements taken during the first extended period and on at least two temperature values obtained from temperature measurements taken during the third extended period.

6. The method according to claim 2 wherein the representative temperature value for the second extended period comprises an average of the at least one first, at least one second and at least one third temperature value.

7. The method according to claim 6 wherein the average is weighted based on the number of measurements taken during the respective first, second and third extended periods, or during time windows specified within those extended periods.

8. The method according to claim 2 wherein each extended period is divided into a plurality of time windows and wherein a representative temperature value is obtained for each time window of each extended period.

9. The method according to claim 2 further comprising calculating the at least one representative temperature value for the second extended period using a temperature value obtained for at least one extended period prior to the first extended period.

10. The method according to claim 2 further comprising filtering the temperature data to disregard faulty or irrelevant data.

11. The method according to claim 2 further comprising correcting at least one non-disregarded temperature reading for diurnal temperature variation.

12. The method according to claim 2 further comprising filtering the temperature measurements prior to calculating the representative temperature values, wherein filtering comprises removing faulty or irrelevant measurements, preferably wherein filtering further comprises removing the maximum and minimum temperature measurements from the measurements obtained during the extended period.

13. The method according to claim 2 further comprising calculating at least one representative temperature value for each at least three, preferably at least five, extended periods.

14. The method according to claim 13 further comprising analyzing the representative temperature values to identify an indication of a temperature change event for the female human user.

15. The method according to claim 14, further comprising providing to the user an indication of timing of an ovulation event based on the identification of the indication of a temperature change event.

16. An apparatus for identifying a temperature change event for a female human user, the apparatus comprising:
 a temperature sensor for obtaining temperature data comprising a plurality of temperature measurements from a female human user during each of a plurality of respective extended periods;
 a communication interface for receiving the temperature data for the female human user for the plurality of extended periods;
 wherein each extended period comprises at least 6 hours, the beginning of one extended period being separated from the beginning of a subsequent and a preceding extended period by at least 18 hours;
 a processor arranged to:
  determine at least one representative temperature value for each extended period based on at least the received temperature data for that extended period;
  assess a plurality of consecutive representative temperature values using a first method to determine whether a temperature change event occurred 4 or more days prior to the extended period; and
  assess a plurality of consecutive representative temperature values using a second method, different from the first method, to determine whether a temperature change event occurred fewer than 4 days prior to the extended period;
 a memory arranged to store a result of the determination of whether a temperature change event occurred 4 or more days prior to the extended period and a result of whether a temperature change event occurred 4 or more days prior to the extended period; and
 an interface arranged to output an indication of a temperature change event.

17. The apparatus according to claim 16 wherein the first method comprises determining the change in representative temperature value from at least one reference value is greater than a predetermined threshold.

18. The apparatus according to claim 16 wherein the first method comprises determining whether consecutive representative temperature values differ by greater than a predetermined threshold value for a plurality of consecutive representative temperature values.

19. The apparatus according to claim 16 wherein the second method comprises assessing the change in the representative temperature values over time against a plurality of criteria.

20. The apparatus according to claim 16 wherein assessing comprises allocating a score to each criterion that is met.

* * * * *